United States Patent
Hyde et al.

(10) Patent No.: US 9,307,829 B2
(45) Date of Patent: *Apr. 12, 2016

(54) GROOMING SYSTEMS, DEVICES, AND METHODS INCLUDING DETECTION OF HAIR-COVERED SKIN LESIONS DURING GROOMING AND INCLUDING TOPOGRAPHICAL ANALYSIS

(71) Applicant: Elwha LLC, Bellevue, WA (US)

(72) Inventors: Roderick A. Hyde, Redmond, WA (US); Gary L. McKnight, Bothell, WA (US)

(73) Assignee: Elwha LLC, Bellevue, WA (US)

( * ) Notice: Subject to any disclaimer, the term of this patent is extended or adjusted under 35 U.S.C. 154(b) by 101 days.

This patent is subject to a terminal disclaimer.

(21) Appl. No.: 14/106,286

(22) Filed: Dec. 13, 2013

(65) Prior Publication Data

US 2015/0164407 A1 Jun. 18, 2015

Related U.S. Application Data

(63) Continuation of application No. 14/106,161, filed on Dec. 13, 2013.

(51) Int. Cl.
*A61B 8/00* (2006.01)
*A46B 15/00* (2006.01)
*A61B 5/00* (2006.01)
(Continued)

(52) U.S. Cl.
CPC ............ *A46B 15/0055* (2013.01); *A45D 24/10* (2013.01); *A46B 9/023* (2013.01); *A46B 15/0004* (2013.01); *A46B 15/0036* (2013.01); *A61B 5/0064* (2013.01); *A61B 5/0071* (2013.01); *A61B 5/0077* (2013.01); *A61B 5/1072* (2013.01); *A61B 5/1079* (2013.01); *A61B 5/444* (2013.01); *A61B 5/6887* (2013.01); *A61B 5/7264* (2013.01); *A61B 5/742* (2013.01); *A61B 5/7405* (2013.01); *A61B 5/7455* (2013.01); *A61B 8/08* (2013.01); *A61B 8/085* (2013.01); *A61B 8/0858* (2013.01); *A61B 8/13* (2013.01); *A61B 8/4455* (2013.01); *A61B 8/4472* (2013.01); *A61B 8/483* (2013.01); *A61B 8/488* (2013.01); *A61B 8/5223* (2013.01); *A61N 7/00* (2013.01); *A46B 2200/1093* (2013.01); *A61B 5/0066* (2013.01); *A61B 5/0075* (2013.01); *A61B 5/0531* (2013.01); *A61B 5/1032* (2013.01);
(Continued)

(58) Field of Classification Search
CPC ...... A46B 15/0055; A45D 24/10; A61B 8/13; A61B 5/7264; A61B 5/0531; A61B 5/444; A61B 5/0075; A61B 5/0064; A61B 5/0066; A61B 5/0071
See application file for complete search history.

(56) References Cited

U.S. PATENT DOCUMENTS 5,016,173 A * 5/1991 Kenet et al. ............... 382/128
5,784,162 A   7/1998 Cabib et al.
(Continued)

OTHER PUBLICATIONS

Aberg et al.; "Electrical impedance spectroscopy and the diagnostic accuracy for malignant melanoma"; Exp Dermatol.; bearing a date of Aug. 2011; 1 page, Abstract Only (pp. 648-652); vol. 20, No. 8; John Wiley & Sons A/S.

Chand et al.; "Microwave Reflectometry as a Novel Diagnostic Method for Detection of Skin Cancers"; IMTC 2005-Instrumentation and Measurement Technology Conference; bearing a date of May 17-19, 2005; pp. 1425-1428; IEEE.

Gu et al.; "Nonlinear fiber-optic strain sensor based on four-wave mixing in microstructured optical fiber"; Optics Letters; bearing a date of Mar. 1, 2012; pp. 794-796; vol. 37, No. 5; Optical Society of America.

Han et al.; "Near-infrared autofluorescence imaging of cutaneous melanins and human skin *in vivo*"; Journal of Biomedical Optics; bearing a date of Mar./Apr. 2009; pp. 024017-1-024017-5; vol. 14, No. 2; Society of Photo-Optical Instrumentation Engineers.

Har-Shai et al.; "Electrical impedance scanning for melanoma diagnosis: a validation study"; Plast Reconstr Surg.; bearing a date of Sep. 2005; 1 page, Abstract Only (pp. 782-790); vol. 116, No. 3.

(Continued)

*Primary Examiner* — Jonathan Cwern

(57) ABSTRACT

Systems, devices, and methods are described for acquiring, among other things, lesion information from a hair or fur-covered region of a biological subject.

37 Claims, 10 Drawing Sheets

(51) Int. Cl.
*A61B 8/08* (2006.01)
*A45D 24/10* (2006.01)
*A61B 8/13* (2006.01)
*A61N 7/00* (2006.01)
*A46B 9/02* (2006.01)
*A61B 5/053* (2006.01)
*A61B 5/103* (2006.01)
*A61B 5/107* (2006.01)

(52) U.S. Cl.
CPC ....... *A61B 5/1077* (2013.01); *A61B 2562/0266* (2013.01); *A61B 2562/046* (2013.01)

(56) References Cited

U.S. PATENT DOCUMENTS

| | | | |
|---|---|---|---|
| 7,386,333 B1* | 6/2008 | Birecki et al. | 600/310 |
| 7,546,156 B2 | 6/2009 | Madden et al. | |
| 2002/0052551 A1 | 5/2002 | Sinclair et al. | |
| 2004/0167421 A1* | 8/2004 | Gregory et al. | 600/547 |
| 2005/0010090 A1 | 1/2005 | Acosta et al. | |
| 2005/0033142 A1 | 2/2005 | Madden et al. | |
| 2007/0238997 A1* | 10/2007 | Camus | 600/437 |
| 2008/0058587 A1 | 3/2008 | Boyden et al. | |
| 2009/0021724 A1 | 1/2009 | Mahadevan-Jansen et al. | |
| 2009/0221919 A1* | 9/2009 | Ben Dor et al. | 600/473 |
| 2009/0299181 A1* | 12/2009 | Ito et al. | 600/440 |
| 2009/0318815 A1 | 12/2009 | Barnes et al. | |
| 2009/0326383 A1 | 12/2009 | Barnes et al. | |
| 2010/0069758 A1 | 3/2010 | Barnes et al. | |
| 2010/0185064 A1 | 7/2010 | Bandic et al. | |
| 2011/0301438 A1* | 12/2011 | Sachse et al. | 600/301 |
| 2012/0265037 A1 | 10/2012 | Bohm et al. | |
| 2015/0164213 A1 | 6/2015 | Hyde et al. | |
| 2015/0164214 A1 | 6/2015 | Hyde et al. | |
| 2015/0164406 A1 | 6/2015 | Hyde et al. | |

OTHER PUBLICATIONS

Koehler et al.; "Non-invasive imaging techniques in the diagnosis of skin diseases"; Expert Opin. Med. Diagn.; bearing a date of 2011; pp. 425-440; vol. 5, No. 5; Informa UK, Ltd.; ISSN 1753-0059.
"Medical Devices, MelaFind ®-P090012"; MELA Sciences, Inc.; bearing a date of Nov. 1, 2011; pp. 1-2; U.S. Food and Drug Administration.
"MelaFind® PMA P090012-Package Insert"; MELA Sciences; bearing a date of Sep. 29, 2010; pp. 1-10.
Monheit et al.; "The Performance of MelaFind: A Prospective Multicenter Study"; Arch Dermatol; bearing a date of Feb. 2011; pp. 188-194; vol. 147, No. 2; American Medical Association.
Oh et al.; "Three-dimensional imaging of skin melanoma *in vivo* by dual-wavelength photoacoustic microscopy"; Journal of Biomedical Optics; bearing a date of May/Jun. 2006; pp. 034032-1-034032-4; vol. 11, No. 3; Society of Photo-Optical Instrumentation Engineers.
Wortsman, Ximena; "Sonography of the Primary Cutaneous Melanoma: A Review"; Radiology Research and Practice; received Jul. 28, 2011; pp. 1-7; vol. 2012, Article ID 814396; Ximena Wortsman; Hindawi Publishing Corporation.
Zonios et al.; "Melanin absorption spectroscopy: new method for noninvasive skin investigation and melanoma detection"; Journal of Biomedical Optics; bearing a date of Jan./Feb. 2008; pp. 014017-1-014017-8; vol. 13, No. 1; Society of Photo-Optical Instrumentation Engineers.

* cited by examiner

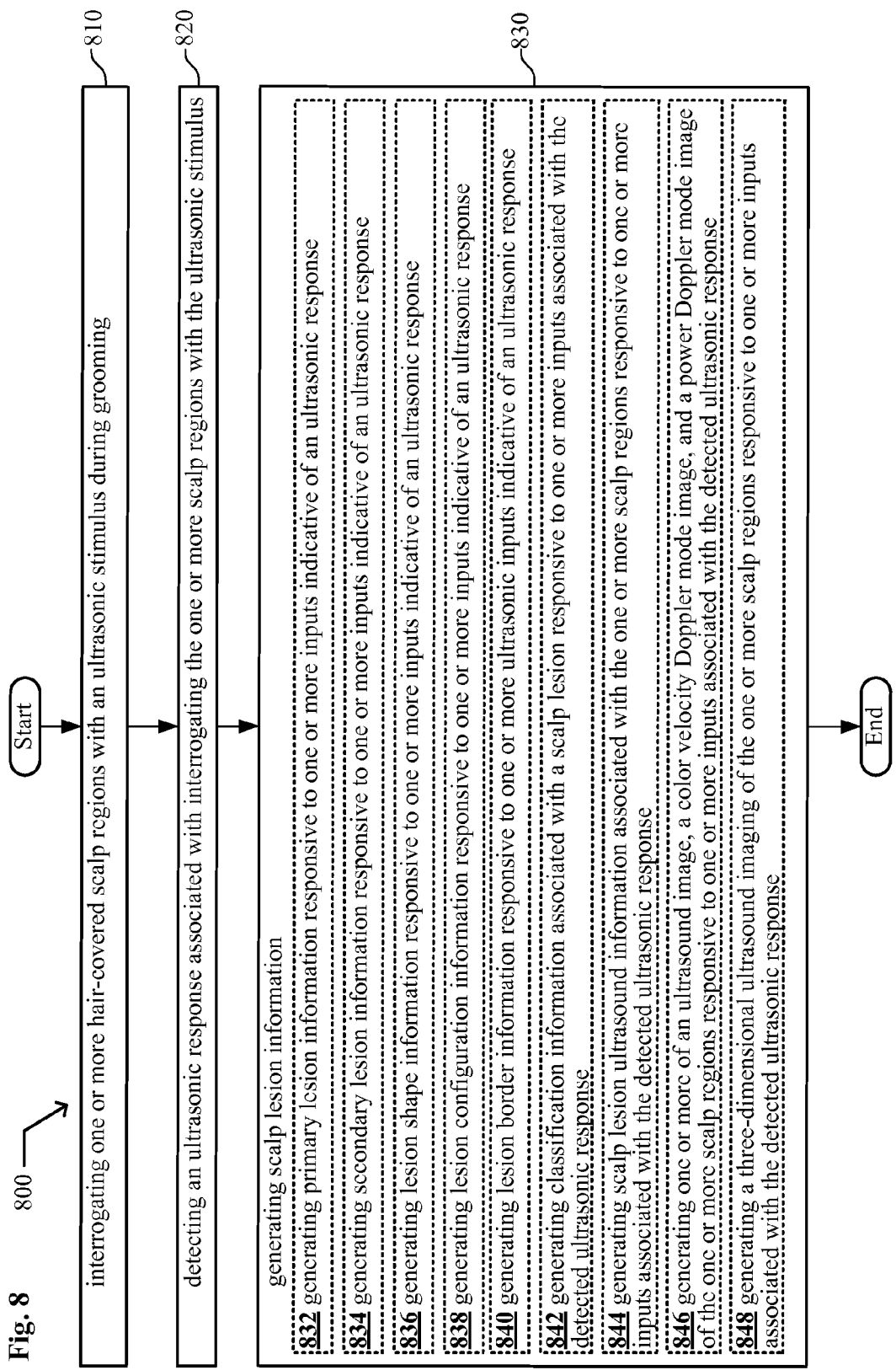

GROOMING SYSTEMS, DEVICES, AND METHODS INCLUDING DETECTION OF HAIR-COVERED SKIN LESIONS DURING GROOMING AND INCLUDING TOPOGRAPHICAL ANALYSIS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

The present application constitutes a continuation of U.S. patent application Ser. No. 14/106,161, entitled GROOMING SYSTEMS, DEVICES, AND METHODS INCLUDING DETECTION OF HAIR-COVERED SKIN LESIONS DURING GROOMING AND INCLUDING TOPOGRAPHICAL ANALYSIS, naming RODERICK A. HYDE AND GARY L. MCKNIGHT as inventors, filed 13, Dec., 2013, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, the present disclosure is directed to, among other things, a grooming system. In an embodiment, the grooming system includes a body structure including a plurality of spaced-apart projections configured to engage hair. In an embodiment, the grooming system includes a sensor array operably coupled to the body structure. In an embodiment, the sensor array is configured to scan a hair-covered scalp region. In an embodiment, the grooming system includes a scalp lesion morphology module operably coupled to the sensor array. In an embodiment, the grooming system includes a scalp lesion dielectric module configured to identify a scalp surface object based on a detected impendence obtained during grooming. In an embodiment, the grooming system includes scalp lesion imaging module configured to identify a scalp surface object based on one or more images of a scalp region obtained during grooming. In an embodiment, the grooming system includes scalp lesion ultrasound imaging module that is operably coupled to one or more ultrasonic transducers and configured to identify a scalp surface object based on one or more ultrasound images of a scalp region obtained during grooming.

In an aspect, the present disclosure is directed to, among other things, a grooming device. In an embodiment, the grooming device includes a comb component having a spine and a plurality of spaced-apart teeth extending outward from the spine. In an embodiment, the grooming device includes circuitry for acquiring surface variations information of a scalp lesion during grooming. In an embodiment, the grooming device includes circuitry for generating classification information associated with a scalp lesion. In an embodiment, the grooming device includes circuitry for negotiating user-specific scalp lesion information based on an authorization protocol. In an embodiment, the grooming device includes circuitry for negotiating user-specific scalp lesion information based on at least one cryptographic protocol, encryption protocol, or decryption protocol. In an embodiment, the grooming device includes circuitry for communicating with a remote enterprise and to receive control command information from the remote enterprise. In an embodiment, the grooming device includes circuitry for actuating a discovery protocol that allows the grooming device and a remote enterprise to identify each other and to negotiate one or more pre-shared keys. In an embodiment, the grooming device includes circuitry for actuating a discovery protocol that allows the grooming device and a remote enterprise to identify each other and negotiate information.

In an aspect, the present disclosure is directed to, among other things, a method including acquiring surface variation information of a hair-covered scalp region. In an embodiment, the method includes generating scalp lesion morphology information based on acquiring surface variation information of the scalp region.

In an aspect, the present disclosure is directed to, among other things, a hair care system. In an embodiment, the hair care system includes a body structure having a plurality of spaced-apart projections configured to engage hair. In an embodiment, one or more of the plurality of spaced-apart projections form part of a dielectric sensor component. In an embodiment, the hair care system includes a scalp lesion dielectric module operably coupled to the dielectric sensor component. In an embodiment, the hair care system is configured to identify a hair-covered scalp lesion based on comparing a detected impedance to reference impedance information stored on one or more memories. In an embodiment, the hair care system includes a hair care protocol module configured to generate scalp region grooming protocol information.

In an aspect, the present disclosure is directed to, among other things, a hairbrush device. In an embodiment, the hairbrush device includes a body structure having a plurality of bristles. In an embodiment, the hairbrush device includes circuitry for acquiring impedance information of one or more scalp regions during grooming. In an embodiment, the hairbrush device includes circuitry for generating scalp lesion information.

In an aspect, the present disclosure is directed to, among other things, a method including acquiring an impedance of one or more hair-covered scalp regions during grooming. In an embodiment, the method includes generating scalp lesion information based on detecting the impedance of one or more scalp regions during grooming.

In an aspect, the present disclosure is directed to, among other things, a grooming system. In an embodiment, the grooming system includes a brush structure having a bristle face and a plurality of bristles extending outward from the bristle face. In an embodiment, the grooming system includes an image sensor component forming part of the brush structure. In an embodiment, the grooming system includes a scalp-imaging module operably coupled to the image sensor component. In an embodiment, the grooming system is configured to generate scalp lesion registration information responsive to one or more inputs from the image sensor component. In an embodiment, the grooming system includes an optical coherence tomography module operably coupled to the image sensor component. In an embodiment, the grooming system includes a scalp lesion location module configured to generate scalp lesion registration information responsive to one or more inputs from the image sensor component.

In an aspect, the present disclosure is directed to, among other things, a hairbrush device. In an embodiment, the hairbrush device includes a brush structure having a bristle face and a plurality of bristles extending outward from the bristle face. In an embodiment, the hairbrush device includes circuitry for acquiring images of one or more scalp regions. In an embodiment, the hairbrush device includes circuitry for generating scalp lesion identification information.

In an aspect, the present disclosure is directed to, among other things, a grooming method. In an embodiment, the grooming method includes acquiring one or more images of a hair-covered scalp region during grooming. In an embodiment, the grooming method includes identifying at least one object in the one or more images. In an embodiment, the grooming method includes generating scalp lesion information responsive to identifying the at least one object in the one or more images. In an embodiment, the grooming method includes determining a scalp disease state responsive to identifying the at least one object in the one or more images. In an embodiment, the grooming method includes storing at least one parameter associated with at least one object indicative of a scalp lesion. In an embodiment, the grooming method includes registering the at least one object using at least one of an artificial body surface marking, a tattoo, or a plurality of nanoparticle fiducial markers.

In an aspect, the present disclosure is directed to, among other things, a hair and scalp care system. In an embodiment, the hair and scalp care system includes a body structure having a plurality of spaced-apart projections configured to engage hair. In an embodiment, the hair and scalp care system includes one or more ultrasonic transducers forming part of the plurality of spaced-apart projections. In an embodiment, the one or more ultrasonic transducers form part of a scalp-contacting portion of the plurality of spaced-apart projections. In an embodiment, the hair and scalp care system includes an ultrasound-imaging module that is operably coupled to one or more ultrasonic transducers forming part of the plurality of spaced-apart projections and that is operable to transmit and receive ultrasound signals associated with a hair-covered region.

In an aspect, the present disclosure is directed to, among other things, a scalp examination device. In an embodiment, the scalp examination device includes a body structure having a plurality of spaced-apart projections configured to engage hair. In an embodiment, the scalp examination device includes circuitry for interrogating one or more scalp regions with an ultrasonic stimulus during grooming. In an embodiment, the scalp examination device includes circuitry for acquiring an ultrasonic response associated with interrogation of one or more scalp regions with the ultrasonic stimulus during grooming. In an embodiment, the scalp examination device includes circuitry for generating lesion classification information associated with the one or more scalp regions responsive to one or more inputs from the circuitry for acquiring an ultrasonic response. In an embodiment, the scalp examination device includes circuitry for generating scalp lesion ultrasound information associated with the one or more scalp regions responsive to one or more inputs from the circuitry for acquiring an ultrasonic response. In an embodiment, the scalp examination device includes circuitry for generating one or more of an ultrasound image, a color velocity Doppler mode image, a power Doppler mode image, and the like, of the one or more scalp regions. In an embodiment, the scalp examination device includes circuitry for generating a three-dimensional ultrasound imaging of the one or more scalp regions during grooming. In an embodiment, the scalp examination device includes circuitry for generating an ultrasound image of the one or more scalp regions responsive to one or more inputs from the circuitry for acquiring an ultrasonic response.

In an aspect, the present disclosure is directed to, among other things, a method including interrogating one or more hair-covered scalp regions with an ultrasonic stimulus during grooming. In an embodiment, the method includes detecting an ultrasonic response associated with interrogating the one or more scalp regions with the ultrasonic stimulus. In an embodiment, the method includes generating scalp lesion information based on a comparison of the detected ultrasonic response and reference scalp ultrasound response information associated with scalp lesions.

BRIEF DESCRIPTION OF THE FIGURES

FIG. 8 shows a flow diagram of a method according to one embodiment.

DETAILED DESCRIPTION

Figure 1:
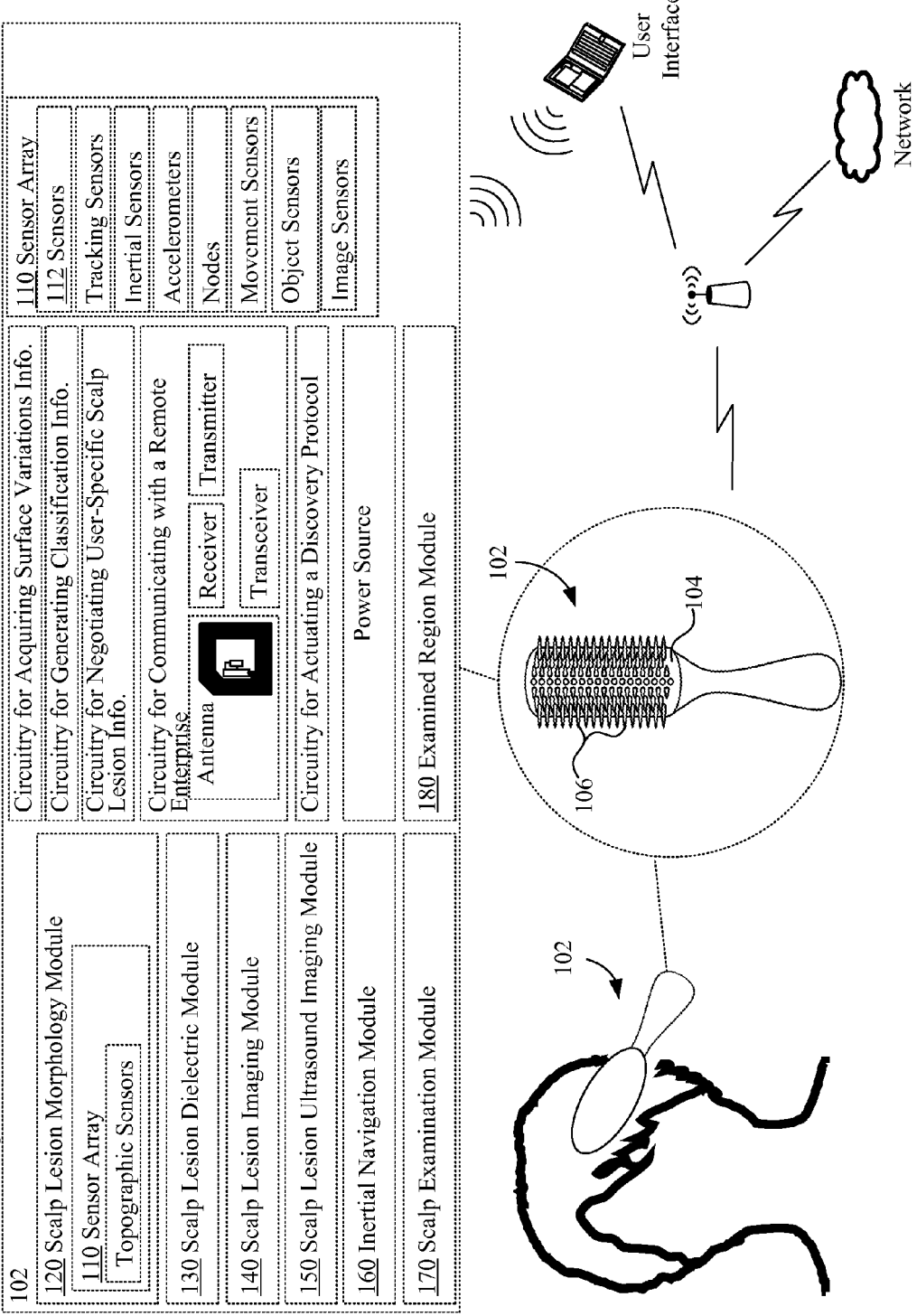
FIG. 1 is a perspective view of a grooming system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Skin cancer can occur on hair-covered regions such as the scalp. For example, skin cancer may appear as a growth, a lesion, a non-healing lesion, a mole, a skin irritation, a sore etc. Non-limiting examples of skin cancer include basal cell skin cancer, squamous cell skin cancer, melanoma, etc. Animals (e.g., vertebrate animals, mammals, pets, dogs, cats, baboons, etc.) can also develop skin cancers including malignant melanomas, mast cell tumors, squamous cell carcinoma, etc.

Regular examination (e.g., self-exams, self-screening, regular screening, etc.) can alert you to changes in your skin and aid in the early detection of skin cancer. While many portions of a subject's skin are exposed and can readily be visually inspected, other portions are covered by hair or fur, and skin lesions, such as skin cancer, can remain hidden for extended periods. Accordingly, scalp examination during hair grooming may help find and identify changes in a growth, a mole, a lesions that does not heal, skin irritations indicated of a cancerous or precancerous condition, and the like. Examination during grooming may increase the chances of detecting certain cancers early by finding or identify new lesions, or changes in lesions, that might be cancerous or precancerous. Early detection of cancer may be implemented using any of various methodologies or technologies described herein.

FIG. 1 shows a grooming system 100 in which one or more methodologies or technologies can be implemented such as, for example, to acquire (assess, calculate, detect, determine, evaluate, gauge, measure, monitor, quantify, receive, resolve, sense, and the like) lesion information from a hair or fur-covered region of a biological subject; to acquire surface variation information of a hair or fur-covered region; to acquire topographic information of a hair or fur-covered region; and the like. For example in an embodiment, during operation, the grooming system 100 is operable to detect surface variation information of a scalp region during grooming; to acquire an impedance of one or more hair-covered scalp regions during grooming; to acquire one or more images of a hair-covered scalp region during grooming; to acquire one or more ultrasonic images of a hair-covered scalp region during grooming; and the like.

In an embodiment, the system 100 includes a grooming device 102. In an embodiment, the grooming device 102 includes a body structure 104 having a plurality of spaced-apart projections 106 configured to engage hair, fur, and the like. In an embodiment, the plurality of spaced-apart projections 106 include a plurality of bristles dimensioned and configured to groom hair, fur, and the like. In an embodiment, the plurality of spaced-apart projections 106 includes a plurality of teeth dimensioned and configured to groom hair, fur, and the like. In an embodiment, the one or more of the plurality of spaced-apart projections 106 include a scalp or biological surface (e.g., hair-covered skin, fur-covered skin, and the like) contact region 108.

In an embodiment, the system 100 includes a sensor array 110 operably coupled to the body structure 104, and configured to scan a hair-covered region of a biological subject. For example, in an embodiment, a sensor array 110 is operably coupled to a grooming device 102 that acquires impedance information associated with one or more hair-covered regions during grooming. In an embodiment, one or more modules compare the acquired impedance information to reference information such as reference information associated with a user, reference lesion information, previously acquired impedance information, and the like. In an embodiment, the one or more modules generate lesion identification information associated with the one or more hair-covered regions interrogated during grooming based on the comparison.

In an embodiment, the system 100 includes a sensor array 110 configured to scan a hair-covered scalp region of a biological subject. In an embodiment, the sensor array 110 includes a topographical sensor array. In an embodiment, the sensor array 110 includes a plurality of sensors 112. Non-limiting examples of sensors 112 include capacitance sensors, contact sensors, fiber optic strain sensors, flexure sensors, image sensors, impedance sensors, movement sensors, nodes, object sensors, optical sensors, pressure sensors, scalp topography sensors, surface roughness sensors, topographic feature sensors, transducers, ultrasonic transducers, and the like. Further non-limiting examples of sensors 112 include accelerometers, inertial sensors, motion sensors, and the like. Further non-limiting examples of sensors 112 include grooming device directional sensors, geographical sensor, inertial navigation sensors, grooming device location sensor, grooming device orientation sensors, tracking sensors, and the like In an embodiment, the sensor array 110 includes one or more one-, two-, or three-dimensional sensor arrays. In an embodiment, one or more of the plurality of spaced-apart projections 106 form part of the sensor array 110.

In an embodiment, the sensor array 110 includes one or more sensor operable to acquire topographic information associated with a hair-covered region of a biological subject. For example, in an embodiment, the sensor array 110 includes a plurality of optical fibers dimensioned and configured to deflect and to generate an output signal responsive to contacting topographic features on a scalp during grooming. In an embodiment, the sensor array 110 includes a plurality of optical fibers forming part of at least one of the plurality of spaced-apart projections and dimensioned and configured to deflect during grooming responsive to contacting topographic features on a scalp. For example, in an embodiment, the sensor array 110 includes a plurality of cantilevers configured to deflect and to generate an output signal responsive to contacting topographic features on a scalp during grooming.

In an embodiment, the sensor array 110 includes a plurality of bristle dimensioned and configured to determine presence of a topographical feature, a lesion, a mole, etc., by deflecting, or to by being displaced along a longitudinal axis responsive to contacting topographic features on a scalp during grooming. For example, during operation, detecting bristles that are similarly deflected displaced may indicate that a user moved the comb closer or further from the scalp. In an embodiment, during operation, dissimilarly deflected or displaced bristles may indicate a presence of a topographical feature, a lesion, a mole, etc. In an embodiment, the sensor array 110 is operable to assess displacement of a bristle relative to one or more neighboring bristles.

In an embodiment, the sensor array 110 includes a plurality of optical fibers configured to mechanically deform and to generate an output signal responsive to contacting topographic features on a scalp during grooming. For example, in an embodiment, the sensor array 110 includes at least one fiber-optic strain sensor for detecting strain-induced changes in the structure and refractive index of a microstructured optical fiber. See e.g., Gu et al., *Nonlinear fiber-optic* Strain *Sensor Based on Four-Wave Mixing in Microstructured Optical Fiber*, Optics Letters, Vol. 37, Issue 5, pp. 794-796 (2012), which is incorporated herein by reference.

In an embodiment, the sensor array 110 includes a plurality of optical fibers having a distribution of lengths that are operable to generate an output signal responsive to contacting topographic features on a scalp during grooming. In an embodiment, the sensor array 110 includes one or more fiber optic strain sensors. In an embodiment, the sensor array 110 includes at least one piezoelectric component operable to generate an output signal responsive to contacting topographic features on a scalp during grooming. In an embodiment, the sensor array 110 includes one or more flexure sensors. In an embodiment, the sensor array 110 includes one or more translation sensors. For example, in an embodiment the sensor array 110 includes one or more translation sensors including components that translate up down and having a tip that contacts the scalp. In an embodiment, the amount of translation is indicative of a distance of the scalp from a reference surface.

In an embodiment, the sensor array 110 includes one or more sensors operable to detect skin contact by one or more of the plurality of spaced-apart projections. For example, in an embodiment, the sensor array 110 includes one or more pressure sensors operable to detect skin contact by one or more of the plurality of spaced-apart projections. In an embodiment, the sensor array 110 includes one or more capacitance sensors operable to detect skin contact by one or more of the plurality of spaced-apart projections. In an embodiment, the sensor array 110 includes one or more flexure sensors operable to detect skin contact by one or more of the plurality of spaced-apart projections. In an embodiment, the sensor array 110 includes one or more strain sensors operable to detect skin contact by one or more of the plurality of spaced-apart projections. In an embodiment, the sensor array 110 is operable to measure surface variations on a scalp as a function of position during grooming.

In an embodiment, the one or more of the plurality of spaced-apart projections 106 include a sensor proximate a scalp contacting region. In an embodiment, the sensor forms part of the sensor array 110. In an embodiment, one or more of the plurality of spaced-apart projections 106 include an optical fiber configured to deflect during grooming responsive to contacting topographic features on a scalp.

In an embodiment, the system 100 includes one or more modules. For example, in an embodiment, the system 100 includes a scalp lesion morphology module 120 operably coupled to the sensor array 110. In an embodiment, a module includes, among other things, one or more computing devices such as a processor (e.g., a microprocessor), a central processing unit (CPU), a digital signal processor (DSP), an application-specific integrated circuit (ASIC), a field programmable gate array (FPGA), and the like, or any combinations thereof, and can include discrete digital or analog circuit elements or electronics, or combinations thereof. In an embodiment, a module includes one or more ASICs having a plurality of predefined logic components. In an embodiment, a module includes one or more FPGAs, each having a plurality of programmable logic components.

For example, in an embodiment, the scalp lesion morphology module 120 includes a module having one or more components operably coupled (e.g., communicatively, electromagnetically, magnetically, ultrasonically, optically, inductively, electrically, capacitively coupled, and the like) to each other. In an embodiment, a module includes one or more remotely located components. In an embodiment, remotely located components are operably coupled, for example, via wireless communication. In an embodiment, remotely located components are operably coupled, for example, via one or more receivers, transmitters, transceivers, antennas, and the like. In an embodiment, the drive control module includes a module having one or more routines, components, data structures, interfaces, and the like.

In an embodiment, a module includes memory that, for example, stores instructions or information. For example, in an embodiment, at least one control module includes memory that stores reference lesion information, examined region information, user-specific lesion information, cumulative lesion information, etc. Non-limiting examples of memory include volatile memory (e.g., Random Access Memory (RAM), Dynamic Random Access Memory (DRAM), and the like), non-volatile memory (e.g., Read-Only Memory (ROM), Electrically Erasable Programmable Read-Only Memory (EEPROM), Compact Disc Read-Only Memory (CD-ROM), and the like), persistent memory, and the like. Further non-limiting examples of memory include Erasable Programmable Read-Only Memory (EPROM), flash memory, and the like. In an embodiment, the memory is coupled to, for example, one or more computing devices by one or more instructions, information, or power buses. For example, in an embodiment, the scalp lesion morphology module 120 includes memory that stores, for example, grooming device inertial information, lesion location information, lesion identification information, bristle displacement information, and the like. In an embodiment, grooming device inertial information may be used to determine the position of a sensed skin lesion, and the scalp lesion morphology module 120 includes memory which stores the skin lesion information in association with position information.

In an embodiment, a module includes one or more computer-readable media drives, interface sockets, Universal Serial Bus (USB) ports, memory card slots, and the like, and one or more input/output components such as, for example, a graphical user interface, a display, a keyboard, a keypad, a trackball, a joystick, a touch-screen, a mouse, a switch, a dial, and the like, and any other peripheral device. In an embodiment, a module includes one or more user input/output components, user interfaces, and the like, that are operably coupled to at least one computing device configured to control (electrical, electromechanical, software-implemented, firmware-implemented, or other control, or combinations thereof) at least one parameter associated with, for example, controlling activating, operating, communicated with a grooming device 102, and the like.

In an embodiment, a module includes a computer-readable media drive or memory slot that is configured to accept signal-bearing medium (e.g., computer-readable memory media, computer-readable recording media, and the like). In an embodiment, a program for causing a system to execute any of the disclosed methods can be stored on, for example, a computer-readable recording medium (CRMM), a signal-bearing medium, and the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, and the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINI-DISC, non-volatile memory card, EEPROM, optical disk, optical storage, RAM, ROM, system memory, web server, and the like.

In an embodiment, a module includes a collection of one or more components that are arranged in a particular manner, or a collection of one or more general-purpose components that may be configured to operate in a particular manner at one or more particular points in time, or also configured to operate in one or more further manners at one or more further times. For example, the same hardware, or same portions of hardware, may be configured or reconfigured in sequential or parallel time(s) as a first type of module (e.g., at a first time), as a second type of module (e.g., at a second time, which may in some instances coincide with, overlap, or follow a first time), or as a third type of module (e.g., at a third time which may, in some instances, coincide with, overlap, or follow a first time or a second time), etc. Reconfigurable or controllable components (e.g., general purpose processors, digital signal processors, field programmable gate arrays, etc.) are capable of being configured as a first module that has a first purpose, then a second module that has a second purpose and then, a third module that has a third purpose, and so on. The transition of a reconfigurable or controllable component may occur in as little as a few nanoseconds, or may occur over a period of minutes, hours, or days.

In some such examples, at the time the component is configured to carry out the second purpose, the component may no longer be capable of carrying out that first purpose until it is reconfigured. A component may switch between configurations as different modules in as little as a few nanoseconds. A component may reconfigure on-the-fly, e.g., the reconfiguration of a component from a first module into a second module may occur just as the second module is needed. A component may reconfigure in stages, e.g., portions of a first module that are no longer needed may reconfigure into the second module even before the first module has finished its operation. Such reconfigurations may occur automatically, or may occur through prompting by an external source, whether that source is another component, an instruction, a signal, a condition, an external stimulus, or similar.

For example, a central processing unit of a personal computer may, at various times, operate as a module for displaying graphics on a screen, a module for writing data to a storage medium, a module for receiving user input, and a module for multiplying two large prime numbers, by configuring its logical gates in accordance with its instructions. Such reconfiguration may be invisible to the naked eye, and in some embodiments may include activation, deactivation, or re-routing of various portions of the component, e.g., switches, logic gates, inputs, or outputs. Thus, in the examples found in the foregoing or following disclosure, if an example includes or recites multiple modules, the example includes the possibility that the same hardware may implement more than one of the recited modules, either contemporaneously or at discrete times or timings. The implementation of multiple modules, whether using more components, fewer components, or the same number of components as the number of modules, is merely an implementation choice and does not generally affect the operation of the modules themselves. Accordingly, it should be understood that any recitation of multiple discrete modules in this disclosure includes implementations of those modules as any number of underlying components, including, but not limited to, a single component that reconfigures itself over time to carry out the functions of multiple modules, or multiple components that similarly reconfigure, or special purpose reconfigurable components.

In an embodiment, the scalp lesion morphology module 120 is configured to access stored data associated with previously measured surface variations by position. In an embodiment, the scalp lesion morphology module 120 is configured to compare the measured surface variations with the previously measured surface variations.

In an embodiment, the sensor array 110 includes one or more sensor elements 112 configured to detect skin contact.

In an embodiment, the scalp lesion morphology module 120 is operable to collect lesion information associated a scalp region responsive to an indication that at least one of the one or more sensor elements 112 is in contact with the scalp region.

In an embodiment, the scalp lesion morphology module 120 is configured to determine a presence of scalp lesions responsive to one or more inputs from the sensor array 110. For example, in an embodiment, the scalp lesion morphology module 120 is configured to determine a change to lesion status by comparing one or more inputs from the sensor array 110 to reference information and determine whether a lesion has undergone any physical changes. In an embodiment, during operation the scalp lesion morphology module 120 compares one or more inputs from the sensor array 110 to reference data to determine whether there has been a morphological change in the scalp region.

In an embodiment, the scalp lesion morphology module 120 is configured to determine a cancer lesion rate of change responsive to a comparison of user-specific reference information to one or more inputs from the sensor array 110. In an embodiment, the scalp lesion morphology module 120 is configured to determine a cancer lesion configuration change responsive to one or more inputs from the sensor array 110. In an embodiment, the scalp lesion morphology module 120 is configured to generate cancer classification information responsive to one or more inputs from the sensor array 110.

In an embodiment, the scalp lesion morphology module 120 module includes a component configured to generate classification information associated with one or more scalp lesions responsive to one or more inputs from the sensor array 110. For example, in an embodiment, the scalp lesion morphology module 120 is configured to generate primary lesion information (e.g., macule, patch, papule, scar, nodule, plaque, wheal, cyst, vesicle, bulla, telangectasias, etc.) responsive to one or more inputs from the sensor array 110. In an embodiment, the scalp lesion morphology module 120 is configured to generate secondary lesion information (e.g., crust, scale, induration, erosion ulceration, atrophy, etc.) responsive to one or more inputs from the sensor array 110.

In an embodiment, the scalp lesion morphology module 120 includes a component configured to generate lesion information. For example, in an embodiment, the scalp lesion morphology module 120 is configured to generate lesion shape information (e.g., annular, round, oval, etc.) responsive to one or more inputs from the sensor array 110. In an embodiment, the scalp lesion morphology module 120 is configured to generate lesion configuration information (e.g., clustered, grouped, linear, dermatomal, etc.) responsive to one or more inputs from the sensor array 110.

In an embodiment, the scalp lesion morphology module is configured to generate lesion asymmetry information responsive to one or more inputs from the sensor array 110. In an embodiment, the scalp lesion morphology module 120 is configured to generate lesion border information responsive to one or more inputs from the sensor array 110. In an embodiment, the scalp lesion morphology module 120 is configured to generate lesion dimension information responsive to one or more inputs from the sensor array 110. In an embodiment, the scalp lesion morphology module 120 is configured to generate lesion rate of change information responsive to one or more inputs from the sensor array 110. In an embodiment, the scalp lesion morphology module 120 is configured to generate topographic information associated with a scalp lesion responsive to one or more inputs from the sensor array 110.

In an embodiment, the scalp lesion morphology module 120 is configured to generate infection information associated with a scalp lesion responsive to one or more inputs from the sensor array 110. In an embodiment, the scalp lesion morphology module 120 is configured to generate scalp texture information responsive to one or more inputs from the sensor array 110. In an embodiment, the scalp lesion morphology module 120 is configured to generate scalp friction information responsive to one or more inputs from the sensor array 110.

In an embodiment, the scalp lesion morphology module 120 is configured to generate combined measurements from the sensor array 110 obtained at different spatial locations. In an embodiment, the scalp lesion morphology module 120 is configured to combine measurements from the sensor array 110 obtained at different spatial locations.

In an embodiment, the scalp lesion morphology module is configured generate scalp surface variation information. For example, in an embodiment, the scalp lesion morphology module is configured generate scalp topographic information. In an embodiment, the scalp lesion morphology module 120 includes at least one of a receiver component, a transceiver component, and a transmitter component operable to communicate with a remote enterprise and to receive control command information from the remote enterprise.

In an embodiment, the scalp lesion morphology module 120 includes at least one of a receiver component, a transceiver component, and a transmitter component operable to communicate lesion information. In an embodiment, the scalp lesion morphology module 120 includes at least one of a receiver, a transceiver, and a transmitter operable to actuate a discovery protocol that allows the scalp lesion morphology module and a remote enterprise to identify each other and to negotiate one or more pre-shared keys.

In an embodiment, the scalp lesion morphology module 120 is configured to generate one or more of a tactile, an audible, and a visual response indicative of the scalp lesion morphology information. In an embodiment, the scalp lesion morphology module 120 is configured to generate one or more of a tactile, an audible, and a visual response indicative of a user instruction (e.g., can ask for a second pass, a slower pass, a static inspection, a re-inspection with different imaging modalities, etc.). In an embodiment, the scalp lesion morphology module 120 is configured to generate one or more of a tactile, an audible, and a visual response indicative of a user instruction to re-groom region. In an embodiment, the scalp lesion morphology module 120 is configured to generate one or more of a tactile, an audible, or a visual response indicative of a user instruction to groom region using a different imaging modality.

In an embodiment, the system 100 includes a scalp lesion dielectric module 130. In an embodiment, the scalp lesion dielectric module 130 is operably coupled to one or more impedance sensors forming part of the sensor array 110 and is configured to identify a scalp surface object based on a detected impendence obtained during grooming.

In an embodiment, the system 100 includes scalp lesion imaging module 140. In an embodiment, the scalp lesion imaging module 140 is operably coupled to one or more image sensors forming part of the sensor array 110 and is configured to identify a scalp surface object based on one or more images of a scalp region obtained during grooming.

In an embodiment, the system 100 includes scalp lesion ultrasound imaging module 150. In an embodiment, the scalp lesion ultrasound imaging module 150 is operably coupled to one or more ultrasonic transducers forming part of the sensor array 110 and is configured to identify a scalp surface object based on one or more ultrasound images of a scalp region obtained during grooming.

In an embodiment, the system 100 includes an inertial navigation module 160 operably coupled to one or more of the plurality of spaced-apart projections. In an embodiment, the inertial navigation module 160 is configured to determine the location of one or more of the plurality of spaced-apart projections with respect to a scalp region location. For example, in an embodiment, the inertial navigation module 160 is operably coupled to one or more accelerometers forming part of the grooming device 102. In an embodiment, the one or more accelerometers are configured to generate information indicative of a location and orientation of the grooming device 102. In an embodiment, the inertial navigation module 160 is operably coupled to one or more gyroscopes of inclinometers forming part of the grooming device 102. In an embodiment, the inertial navigation module 160, can use differential acceleration data from two or more accelerometers, or can use data from gyroscopes, to determine changes in orientation of the grooming device 102. In an embodiment, the inertial navigation module 160 can use accelerometers, inclinometers, and/or gyroscopes oriented along multiple axes in order to determine multi-axis location and orientation information for the grooming device 102. In an embodiment, the inertial navigation module 160 can integrate information relating to changes in location or orientation of grooming device 102 to determine the location or orientation of grooming device 102 relative to a reference location or orientation, or relative to a previous location and orientation of grooming device 102. In an embodiment, information regarding the location and orientation of a portion of grooming device 102, e.g., body structure 104, can be combined with information on the location, length, and orientation of a projection, bristle or tooth skin lesion relative to the portion of grooming device 102 can be used to determine the position of the tip of the projection, bristle, or tooth. In an embodiment, information regarding the location and orientation of grooming device 102, can be combined with information on the location and orientation of a skin lesion relative to grooming device 102 can be used to determine the position of the skin lesion on the scalp.

In an embodiment, the system 100 includes a scalp examination module 170 that determines cumulative lesion examination information based on the at least one measurand output from the sensor array 110. In an embodiment, the system 100 includes a scalp examination module 170 that is configured to track of the location of examined regions, and determines which locations have not been examined. For example, in an embodiment, the system 100 includes a scalp examination module 170 that is configured to track of the location of examined regions based on one or more measurands outputs from an inertial sensor. In an embodiment, the scalp examination module 170 includes one or more memories configured to store at least one of lesion-specific examination information, user-specific lesion examination history, or previous-in-time lesion examination history. In an embodiment, the scalp examination module 170 includes one or more components configured to initiate a next-in-time lesion examination protocol based on determining whether a lesion or a regions has been previously examined. In an embodiment, the scalp examination module 170 tracks the locations of lesions on the hair-covered regions based on inertial information. In an embodiment, the grooming region module is configured to track cumulative motion of a grooming device 102 relative to the one or more lesions using motion tracking. In an embodiment, the scalp examination module 170 is operable to detect a marker previously released by the marker-dispenser component.

In an embodiment, the system 100 includes an examined region module 180 operably coupled to one or more marker-dispenser components. In an embodiment, during operation, the examined region module 180 is configured to activate release of one or more particles to mark scalp regions. In an embodiment, during operation, the examined region module 180 is operable to activate release of a dye (e.g., a hair dye, a temporary dye, a short-term dye, a florescent dye, etc.) to mark which regions have been examined, so that a user knows what has and has not been examined. In an embodiment, during operation, the examined region module 180 is operable to activate release of a marker particle (e.g., a magnetic particle, a conductive particle, a florescent particle, etc.) to mark which regions have been examined, so that a user knows what has and has not been examined. In an embodiment, the examined region module 180 is operable to activate release of the marker (e.g., dye or particle) from the to one or more marker-dispenser components based on a determination that the region has been examined. In an embodiment, the examined region module 180 is operable to detect a marker previously released by the marker-dispenser component. In an embodiment, the sensor array 110 is operable to modify a scan pattern based on detection of the marker. In an embodiment, the examined region module 180 is configured to generate one or more of a tactile, an audible, and a visual response indicative of detection of the marker. In an embodiment, the examined region module 180 is configured to activate release of one or more particles to mark scalp regions. In an embodiment, the examined region module 180 is operable to detect a marker previously released by the marker-dispenser component. In an embodiment, the examined region module 180 is configured to activate release of one or more particles to mark scalp regions. In an embodiment, the examined region module 180 is operable to detect a marker previously released by the marker-dispenser component.

In an embodiment, the one or more marker-dispenser components are operably coupled to one or more of the plurality of spaced-apart projections. In an embodiment, the examined region module 180 is operable to activate release from one or more of the plurality of spaced-apart projections operably coupled to one or more marker-dispenser components. In an embodiment, the examined region module 180 is operable to release markers (e.g., dye or particles) uniformly within an inspected region, along the borders of an inspected region, at skin lesions, etc. In an embodiment, the markers may be applied to the scalp region. In an embodiment, the markers may be applied to hair or fur covering a scalp region. In an embodiment, the examined region module 180 is operable to detect previously released markers to determine that a region has been previously inspected. In an embodiment, the system 100 includes an inertial navigation module operably coupled to the body structure 104.

Figure 2:
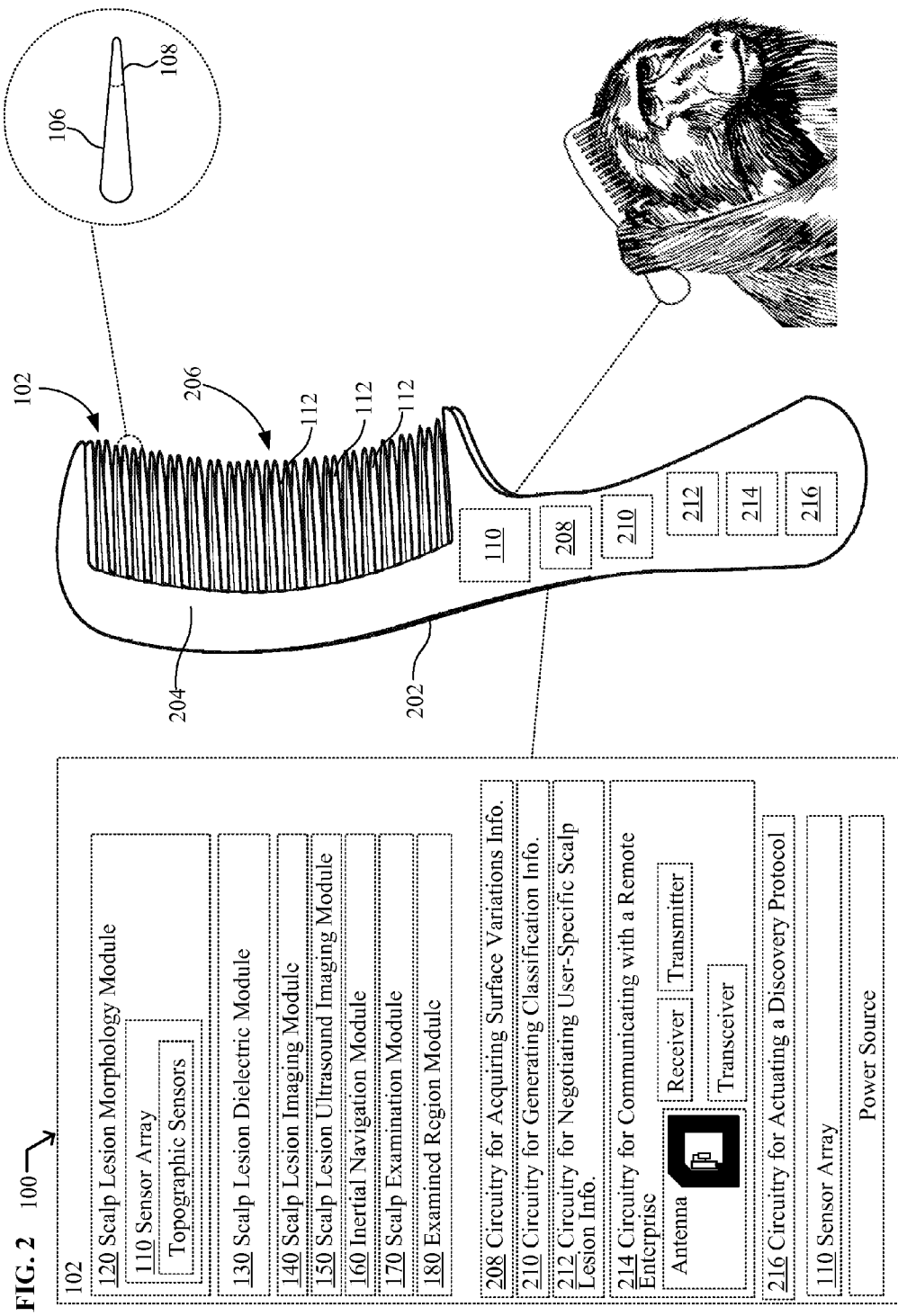
FIG. 2 is a perspective view of a hair care system according to one embodiment.

Referring to FIG. 2, in an embodiment, the system 100 includes a grooming device 102. In an embodiment, the grooming device 102 includes a comb component 202 including a spine 204 having a plurality of spaced-apart teeth 206 extending outward from the spine 204.

In an embodiment, the grooming device 102 includes circuitry 208 for acquiring surface variations information of a scalp lesion during grooming. For example, in an embodiment, the circuitry 208 for acquiring surface variations information is operably coupled to at least one fiber-optic strain sensor that detects strain-induced changes in the structure and refractive index of a microstructured optical fiber responsive to contacting topographic variations on a scalp. In an embodiment, the grooming device 102 includes circuitry 210 for generating classification information associated with the scalp lesion. In an embodiment, the circuitry 208 for acquiring surface variations information is operably coupled to one or more sensors forming part of at least one of the plurality of spaced-apart teeth. In an embodiment, the circuitry 208 for acquiring surface variations information is operably coupled to at least one sensor proximate a scalp-contacting region of the plurality of spaced-apart teeth. In an embodiment, the circuitry 208 for generating classification information associated with the scalp lesion is configured to generate cancer classification information responsive from one or more inputs from the circuitry 208 for acquiring surface variations information.

In an embodiment, the circuitry 210 for generating classification information associated with the scalp lesion is configured to generate classification information responsive to one or more inputs indicative of a lesion shape. In an embodiment, the circuitry 210 for generating classification information associated with the scalp lesion is configured to generate classification information responsive to one or more inputs indicative of a lesion configuration. In an embodiment, the circuitry 210 for generating classification information associated with the scalp lesion is configured to generate classification information responsive to one or more inputs indicative of a lesion asymmetry. In an embodiment, the circuitry 210 for generating classification information associated with the scalp lesion is configured to generate classification information responsive to one or more inputs indicative of a lesion border configuration.

In an embodiment, the circuitry 210 for generating classification information associated with the scalp lesion is configured to generate classification information responsive to one or more inputs indicative of a lesion. In an embodiment, the circuitry 210 for generating classification information associated with the scalp lesion is configured to generate classification information responsive to one or more inputs indicative of a lesion rate of change.

In an embodiment, the grooming device 102 includes circuitry 212 for negotiating user-specific scalp lesion information based on at least one authentication protocol. For example, in an embodiment, the grooming device 102 includes circuitry 212 for negotiating user-specific scalp lesion information based on at least one cryptographic protocol, encryption protocol, or decryption protocol. In an embodiment, the grooming device 102 includes circuitry 214 for communicating with a remote enterprise and to receive control command information from the remote enterprise. For example, in an embodiment, circuitry 214 for communicating with a remote enterprise is operably coupled to one or more transceivers, transmitters, or receivers configured to communicating with a remote enterprise and to receive control command information from the remote enterprise.

In an embodiment, the grooming device 102 includes circuitry 216 for actuating a discovery protocol that allows the grooming device and a remote enterprise to identify each other and to negotiate one or more pre-shared keys. In an embodiment, the grooming device 102 includes circuitry 216 for actuating a discovery protocol that allows the system 100 and a remote enterprise to identify each other and negotiate information.

In an embodiment, the grooming device 102 includes a power source. In the power source is operably coupled to one or more components, modules, circuitry, sensors, and the like. In an embodiment, the power source is configured to power one or more components, modules, circuitry, sensor, and the like. In an embodiment, the power source is electromagnetically, magnetically, acoustically, optically, inductively, electrically, or capacitively coupled to one or more components, modules, circuitry, sensors, and the like. For example, in an embodiment, the power source is electromagnetically, magnetically, acoustically, optically, inductively, electrically, or capacitively coupled to one or more modules.

Non-limiting examples of power sources examples include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, and the like. Further non-limiting examples of power sources include one or more generators (e.g., electrical generators, thermo energy-to-electrical energy generators, mechanical-energy-to-electrical energy generators, micro-generators, nano-generators, and the like) such as, for example, thermoelectric generators, piezoelectric generators, electromechanical generators, biomechanical-energy harvesting generators, and the like. In an embodiment, the power source includes at least one rechargeable power source. In an embodiment, the grooming device 102 carries the power source. In an embodiment, grooming device 102 includes at least one of a battery, a capacitor, or a mechanical energy store (e.g., a spring, a flywheel, and the like).

In an embodiment, the power source is configured to wirelessly receive power from a remote power supply. For example, in an embodiment, the power source receives power from a remote power supply via one or more transceivers or receivers. In an embodiment, the power source is configured to wirelessly receive power via at least one of an electrical conductor or an electromagnetic waveguide. In an embodiment, power source includes at least one of a thermoelectric generator, a piezoelectric generator, a microelectromechanical systems generator, or a biomechanical-energy harvesting generator.

Figure 3:
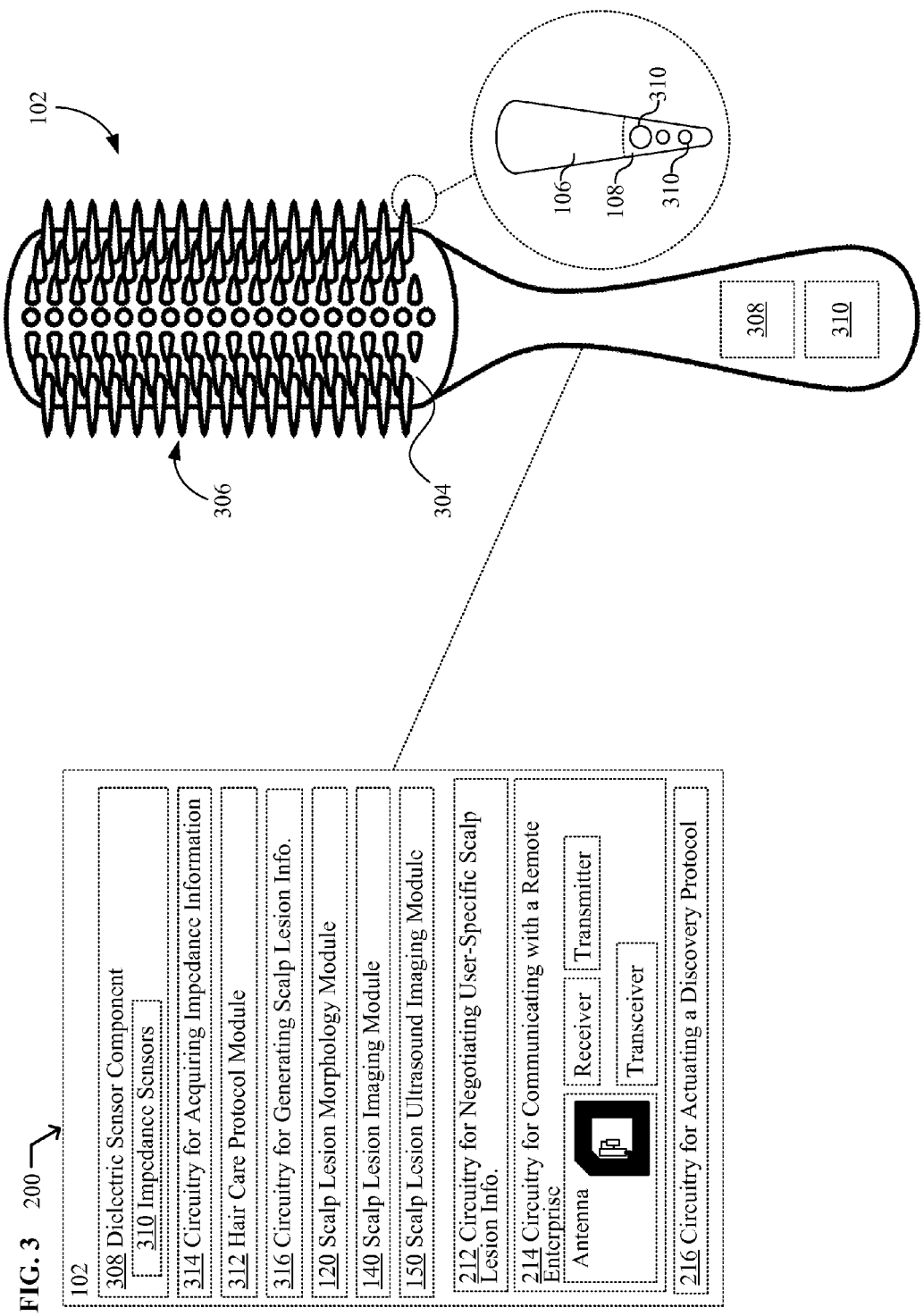
FIG. 3 is a perspective view of grooming system according to one embodiment.

FIG. 3 shows a hair care system 200 in which one or more methodologies or technologies can be implemented such as, for example, acquiring impedance information of one or more hair-covered regions, fur-covered regions, and the like, during grooming. In an embodiment, the hair care system 200 includes a grooming device 102 having body structure 304 including a plurality of spaced-apart projections 306 configured to engage hair.

In an embodiment, the grooming device 102 includes a dielectric sensor component 308. In an embodiment, one or more of the plurality of spaced-apart projections 306 form part of a dielectric sensor component 308. In an embodiment, the dielectric sensor component 308 includes one or more impedance sensors configured to measure impedance associated with a scalp region between two proximate spaced-apart projections 306.

In an embodiment, the dielectric sensor component 308 is configured to acquire impedance information of one or more hair-covered scalp regions during grooming. See e.g., Har-Shai, et al., *Electrical Impedance Scanning for Melanoma Diagnosis: A Validation Study*, Plast Reconstr Surg. 2005 September; 116(3):782-90, doi: 10.1097/01.prs.0000176258.52201.22, which is incorporated herein by reference. For example, in an embodiment, the dielectric sensor component 308 includes one or more impedance sensors 310 for acquiring impedance information from one or more hair-covered scalp regions as hair is being groomed. In an embodiment, the dielectric sensor component 308 is configured to detected impedance of one or more hair-covered scalp regions as hair is being combed or brushed. In an embodiment, the dielectric sensor component 308 is configured to detected impedance of one or more hair-covered scalp regions as hair is being parted.

In an embodiment, the hair care system 200 includes a scalp lesion dielectric module 130 operably coupled to the dielectric sensor component 308. In an embodiment, the scalp lesion dielectric module 130 is configured to identify a scalp surface object based on a comparison of a detected impendence to reference scalp surface object impedance information. In an embodiment, the scalp lesion dielectric module 130 is configured to identify a scalp surface object based on a detected impendence as function of frequency. See e.g., Aberg, et al., *Electrical impedance spectroscopy and the diagnostic accuracy for malignant melanoma*, Exp Dermatol. 2011 August; 20(8):648-52. doi: 10.1111/j.1600-0625.2011.01285.x. Epub 2011 May 4, which is incorporated herein by reference.

In an embodiment, the scalp lesion dielectric module 130 is configured to identify a scalp surface object based on a detected impendence as a function of position during grooming. In an embodiment, the scalp lesion dielectric module 130 is configured to acquire impedance information associated with one or more hair-covered regions or fur-covered regions. In an embodiment, the scalp lesion dielectric module 130 is configured to acquire dielectric permittivity information associated with one or more scalp regions during grooming. In an embodiment, the scalp lesion dielectric module 130 is configured to acquire conductivity information associated with one or more scalp regions during grooming.

In an embodiment, the scalp lesion dielectric module 130 is configured to generate at least one of a lesion location, a lesion composition, a lesion configuration, or lesion shape based on an acquired impendence. In an embodiment, the scalp lesion dielectric module 130 is configured to generate lesion identification information based on an acquired impendence.

In an embodiment, the scalp lesion dielectric module 130 is configured to generate scalp lesion classification information based on an acquired impendence. In an embodiment, the scalp lesion dielectric module 130 is configured to generate scalp lesion information based on a comparison between at least one datum associated with a detected anatomical feature of the scalp and reference scalp impedance information. In an embodiment, the scalp lesion dielectric module 130 is configured to access stored data associated with previously measured surface impedance by position. In an embodiment, the scalp lesion dielectric module 130 is configured to compare detected impedance of the scalp with previously detected impendence information.

In an embodiment, hair care system 200 includes a hair care protocol module 312. In an embodiment, the hair care protocol module 312 is configured to generate next-in-time scalp region grooming protocol information. In an embodiment, the hair care protocol module 312 is configured to generate next-in-time scalp region detection regimen information. In an embodiment, the hair care protocol module 312 is configured to generate scalp region detection regimen information. In an embodiment, the hair care protocol module 312 is configured to generate scalp region inspection regimen information. In an embodiment, the hair care module 312 is configured to generate scalp region grooming regimen information.

In an embodiment, the grooming device 102 takes the form of a hairbrush device (see e.g., FIG. 3). In an embodiment, the hairbrush device includes a body structure 304 having a plurality of bristles. In an embodiment, the grooming device 102 is configured to measure impedance associated with a scalp region between two proximate bristles 306. For example, in an embodiment, the grooming device 102 includes a dielectric sensor component 308 having a plurality of impedance sensors forming part of one or more of the plurality of bristles.

In an embodiment, the grooming device 102 includes circuitry 314 for acquiring impedance information of one or more scalp regions during grooming. In an embodiment, the circuitry 314 for acquiring impedance information of one or more scalp regions includes one or more impedance sensors. In an embodiment, the circuitry 314 for acquiring impedance information of one or more scalp regions includes one or more impedance sensors forming part of the plurality of bristles. In an embodiment, the circuitry 314 for acquiring impedance information of one or more scalp regions during grooming is operably coupled to one or more impedance sensors forming part of at least one of the plurality of bristles 306.

In an embodiment, the grooming device 102 includes circuitry 316 for generating scalp lesion information. In an embodiment, the circuitry 316 for generating scalp lesion information includes circuitry for generating lesion classification information responsive to one or more inputs from an impedance sensor. In an embodiment, the circuitry 316 for generating scalp lesion information includes circuitry for generating scalp surface object identification information responsive to a detected change in impedance. In an embodiment, the circuitry 316 for generating scalp lesion information includes circuitry for generating impedance information associated with one or more scalp regions during grooming.

In an embodiment, the circuitry 316 for generating scalp lesion information includes circuitry for generating dielectric permittivity information associated with one or more scalp regions during grooming. In an embodiment, the circuitry 316 for generating scalp lesion information includes circuitry for generating at least one of a lesion location, a lesion composition, a lesion configuration, or lesion shape based on a detected impendence. In an embodiment, the circuitry 316 for generating scalp lesion information includes circuitry for generating scalp lesion classification information responsive to a detected impendence. In an embodiment, the circuitry 316 for generating scalp lesion information includes circuitry for generating scalp lesion information based on a comparison between a detected impedance associated with an anatomical feature of at least one scalp region and reference scalp impedance information.

Figure 4:
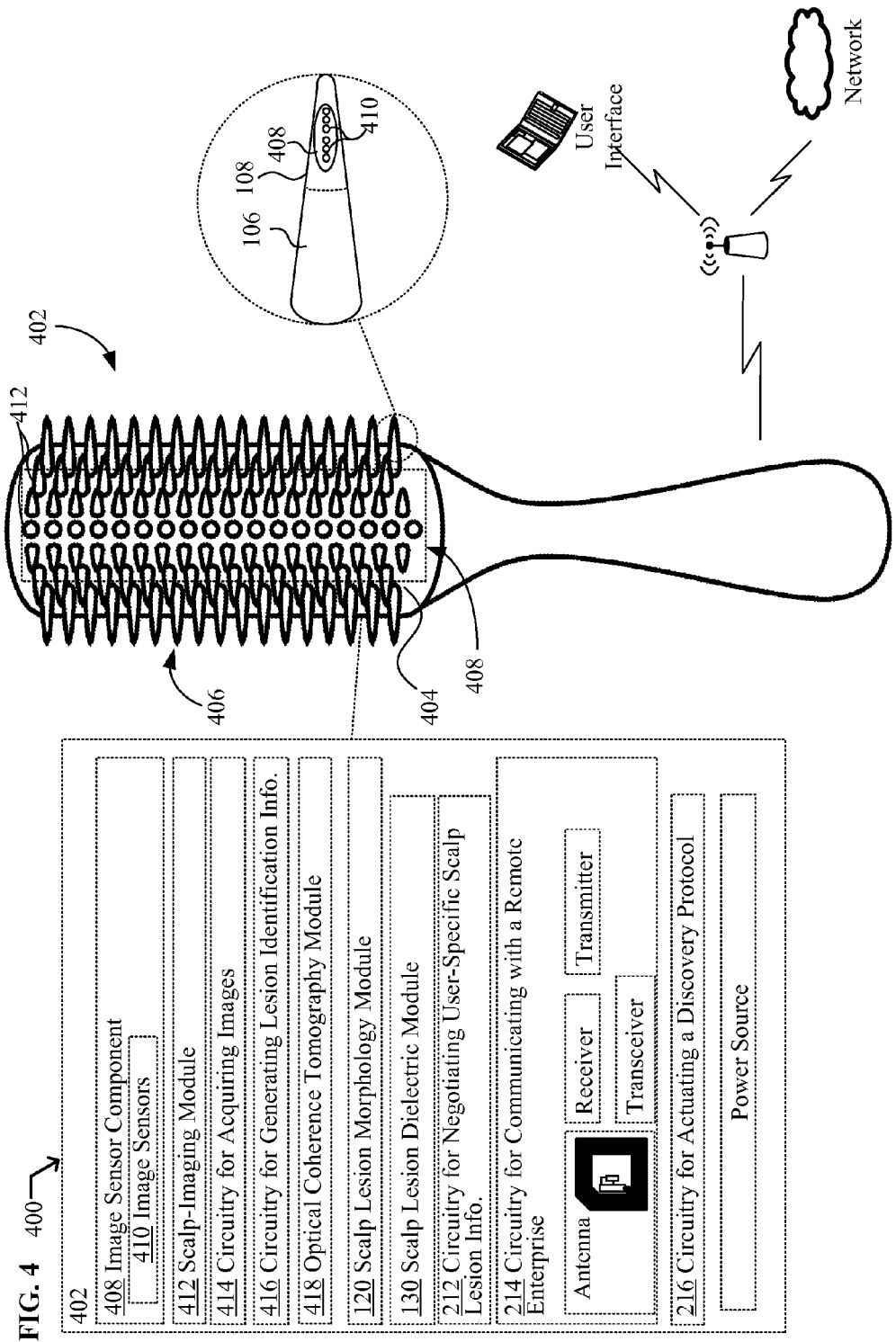
FIG. 4 is a perspective view of a hair and scalp care system according to one embodiment.

FIG. 4 shows a grooming system 400 in which one or more methodologies or technologies can be implemented such as, for example, acquiring image information of one or more hair-covered regions, fur-covered regions, and the like, during grooming. In an embodiment, the grooming system 400 includes a brush structure 402 having a bristle face 404 and a plurality of bristles 406 extending outward from the bristle face 404. In an embodiment, the grooming system 400 includes an image sensor component 408 forming part of the brush structure 402.

In an embodiment, the grooming system 400 is configured to identify a scalp surface object based on one or more images of one or more scalp regions, hair-covered regions, fur-covered regions, and the like, obtained during grooming. For example, in an embodiment, the brush structure 402 is operably coupled to an image sensor component 408 that acquires image information associated with one or more hair-covered regions during grooming. In an embodiment, one or more modules compare the acquired image information to reference image information such as reference image information associated with a user, reference lesion image information, previously acquired image information, and the like. In an embodiment, the one or more modules generate lesion identification information associated with the one or more hair-covered regions imaged during grooming based on the comparison.

In an embodiment, the image sensor component 408 includes one or more image sensors 410. In an embodiment, the image sensor component 408 includes one or more optical image sensors. For example, in an embodiment, the image sensor component 408 includes one or more spectrometers. Non-limiting examples of spectrometers include imaging spectrometers, photo-acoustic imaging spectrometers, thermo-acoustic imaging spectrometers, photo-acoustic/thermo-acoustic tomographic imaging spectrometers, ultrasound spectrometers, and the like In an embodiment, the image sensor component 408 is configured to detect at least one of an emitted energy or a remitted energy associated with a hair-covered region, a fur-covered region, and the like. In an embodiment, image sensor component 408 is configured to detect an optical energy absorption profile of a portion of a hair-covered region. In an embodiment, image sensor component 408 is configured to detect an optical energy emission profile of a portion of a hair-covered region. In an embodiment, the image sensor component 408 includes at least one time delay and integration (TDI) charge-coupled device (CCD). In an embodiment, the image sensor component 408 includes at least one complementary metal-oxide-semiconductor (CMOS) image sensor. In an embodiment, the image sensor component 408 includes at least one a variable-integration-time image sensor. In an embodiment, the image sensor component 408 includes at least one of a time-integrating optical component, a linear time-integrating component, a nonlinear optical component, a temporal autocorrelating component, a variable-integration-time image sensor component, and the like.

In an embodiment, the image sensor component 408 is configured to detect an excitation radiation and an emission radiation associated with a portion of a hair-covered region, a fur-covered region, and the like. For example, in an embodiment, the image sensor component 408 includes one or more image sensors 410 operable to detect at least one of an emitted energy or a remitted energy associated with a portion of a hair-covered scalp region.

In an embodiment, one or more of the plurality of bristles 406 form part of the image sensor component 408. For example, in an embodiment, one or more of the plurality of bristles 406 form part of an optical image sensor. In an embodiment, one or more of the plurality of bristles 406 comprises an optical fiber. In an embodiment, the optical fiber is configured to transmit illumination light from an illumination source coupled to the brush structure 402 to a distal end proximate the scalp. In an embodiment, the illumination light may be broad-band, monochromatic, cover a specified spectral band, have a specified polarization, etc. In an embodiment, the optical fiber is configured to receive backscattered light from a scalp region and transmit the light to an optical sensor coupled to the brush structure 402. In an embodiment, at least a portion of the image sensor component 408 is located proximate a distal end of one or more of the plurality of bristles 406. In an embodiment, at least a portion of the image sensor component 408 is located proximate a scalp contact region 108 of the one or more of the plurality of bristles 406.

In an embodiment, the image sensor component 408 includes at least one illumination component and at least one image sensor component 408 and is configured to measure one or more of a spectral reflectance, a polarization, and a fluorescence of a scalp region. In an embodiment, the image sensor component 408 is operable to acquire one or more images of a hair-covered scalp region during grooming. In an embodiment, the image sensor component 408 is operable to acquire backscattered light from a scalp region during grooming. In an embodiment, the image sensor component 408 is operable to acquire one or more optical coherence tomography images of a scalp region during grooming.

In an embodiment, the grooming system 400 includes a scalp-imaging module 412 operably coupled to the image sensor component 408. In an embodiment, the scalp-imaging module 412 is operable to generate a spatial map of a scalp region by combining images from the image sensor component 408 obtained at different spatial locations during grooming. For example, in an embodiment, the scalp-imaging module 412 includes circuitry configured to generate a spatial map of a scalp region by combining images from the image sensor component 408 obtained at different spatial locations during grooming. In an embodiment, the grooming system 400 includes a scalp-imaging module 412 configured to generate scalp lesion registration information responsive to one or more inputs from the image sensor component. In an embodiment, the scalp-imaging module 412 is operable to store multi-pass information associated with scalp images obtained at different times during grooming.

In an embodiment, the scalp-imaging module 412 is operable to generate lesion color information responsive to one or more inputs from the image sensor component. In an embodiment, the scalp-imaging module 412 is operable to generate classification information associated with the scalp lesion responsive to one or more inputs from the image sensor component 408 indicative of a lesion color. In an embodiment, the grooming system 400 includes a scalp lesion location module 412 configured to generate scalp lesion registration information responsive to one or more inputs from the image sensor component.

Referring to FIG. 4, in an embodiment, a hair-brushing device includes a brush structure 402 having a bristle face 404 and a plurality of bristles 406 extending outward from the bristle face 404. In an embodiment, the hairbrush device includes circuitry 414 for acquiring images of one or more scalp regions.

In an embodiment, the circuitry 414 for acquiring images is operably coupled to an image sensor component 408 forming part of brush structure 402. In an embodiment, one or more of the plurality of bristles 406 form part of an image sensor component 408 operably coupled to the circuitry 414 for acquiring images of one or more scalp regions. In an embodiment, one or more of the plurality of bristles 406 include a scalp contact region 108 that forms part of an image sensor component 408 operably coupled to the circuitry 414 for acquiring images of one or more scalp regions.

In an embodiment, the circuitry 414 for acquiring images forms part of the brush structure 402. In an embodiment, the circuitry 414 for acquiring images is operable to generate lesion information representative of a parameter associated with a location and a dimension of at least one scalp lesion responsive to one or more inputs from the image sensor component 408. In an embodiment, the circuitry 414 for acquiring images is operable is operable to generate scalp lesion information responsive to one or more inputs from the image sensor component 408. In an embodiment, the circuitry 414 for acquiring images is operable to determine a scalp disease state responsive to identifying at least one object in an image from the image sensor component 408.

In an embodiment, the hairbrush device includes circuitry 416 for generating lesion identification information. In an embodiment, the circuitry 416 for generating lesion identification information includes circuitry for generating scalp lesion identification information. In an embodiment, the circuitry 416 for generating lesion identification information includes one or more memories configured to store scalp lesion identification information. In an embodiment, the circuitry 416 for generating scalp lesion identification information is operable to identify groups of pixels in an image indicative of a lesion color. In an embodiment, the circuitry 416 for generating scalp lesion identification information is operable to generate classification information responsive to one or more inputs from the circuitry for acquiring images of one or more scalp regions indicative of a lesion color. In an embodiment, the circuitry 416 for generating scalp lesion identification information is operable to generate lesion color information responsive to one or more inputs from the circuitry for acquiring images of one or more scalp regions. In an embodiment, the circuitry 416 for generating scalp lesion identification information is operable to identify groups of pixels in an image indicative of at least one scalp lesion.

In an embodiment, the grooming system 400 includes an optical coherence tomography module 418 operably coupled to the image sensor component 408. In an embodiment, the optical coherence tomography module 418 is configured to generate a cross-sectional tomographic imaging of one or more scalp regions imaged during grooming.

In an embodiment, the grooming system 400 includes a scalp lesion morphology module 120. In an embodiment, the scalp lesion morphology module 120 is operably coupled to one or more topographic sensors forming part of the brush structure 402. In an embodiment, the scalp lesion morphology module 120 is configured to determine a presence of scalp lesions responsive to one or more inputs from the one or more topographic sensors. In an embodiment, the grooming system 400 includes a scalp lesion dielectric module 130. In an embodiment, the scalp lesion dielectric module 130 is operably coupled to one or more impedance sensors forming part of the brush structure 402 and is configured to identify a scalp surface object based on a detected impendence obtained during grooming. In an embodiment, the grooming system 400 includes scalp lesion ultrasound imaging module 150. In an embodiment, the scalp lesion ultrasound imaging module 150 is operably coupled to one or more ultrasonic transducers forming part of the sensor array 110 and is configured to identify a scalp surface object based on one or more ultrasound images of a scalp region obtained during grooming In an embodiment, the grooming system 400 includes circuitry 212 for negotiating user-specific scalp lesion information based on at least one authentication protocol. For example, in an embodiment, the grooming system 400 includes circuitry 212 for negotiating user-specific scalp lesion information based on at least one cryptographic protocol, encryption protocol, or decryption protocol. In an embodiment, the grooming device 402 includes circuitry 214 for communicating with a remote enterprise and to receive control command information from the remote enterprise In an embodiment, the grooming system 400 includes circuitry 216 for actuating a discovery protocol that allows the grooming device and a remote enterprise to identify each other and to negotiate one or more pre-shared keys. In an embodiment, the grooming system 400 includes circuitry 216 for actuating a discovery protocol that allows the system and a remote enterprise to identify each other and negotiate information.

Figure 5:
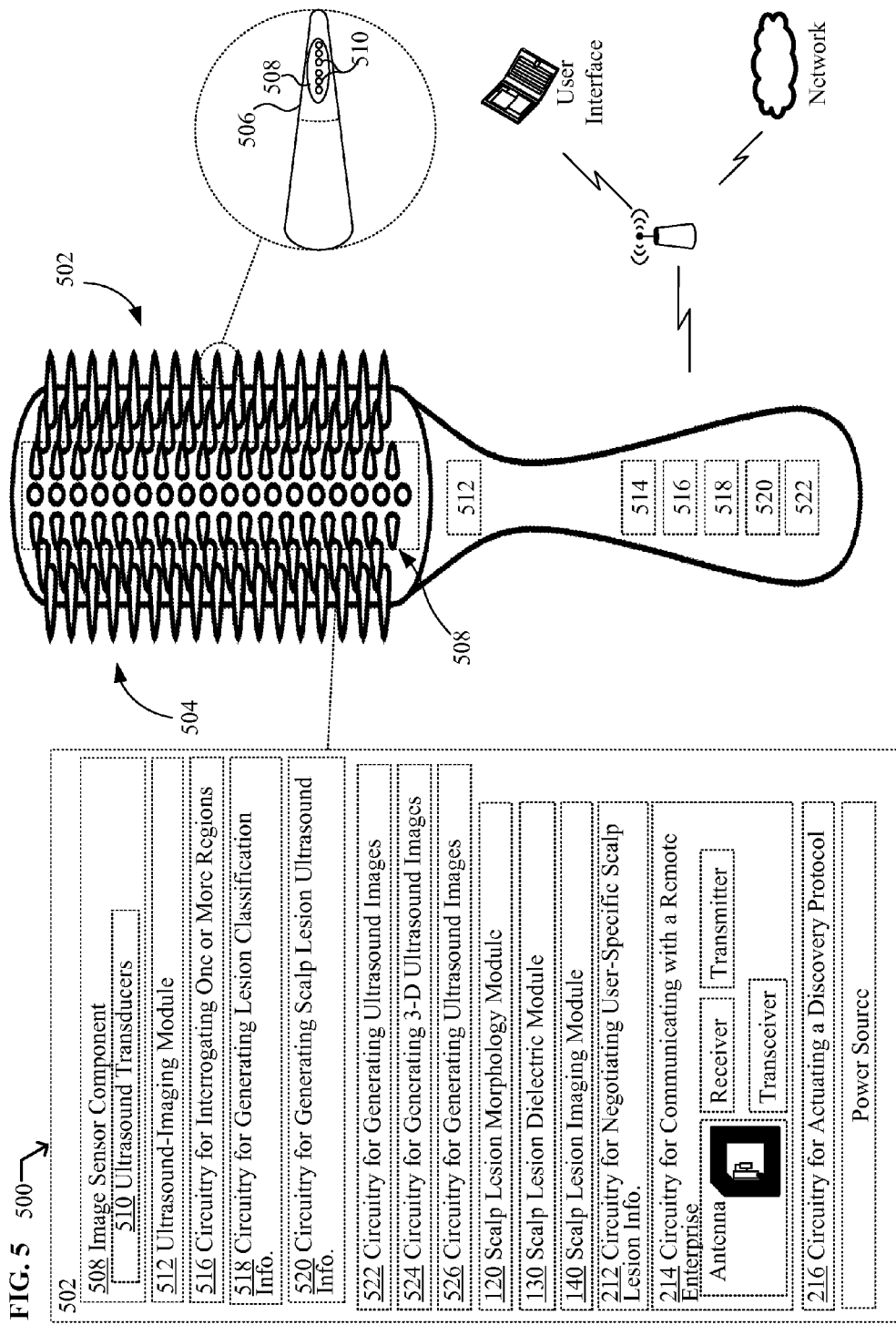
FIG. 5 is a perspective view of a hair and scalp care system according to one embodiment.

FIG. 5 shows a hair and scalp care system 500 in which one or more methodologies or technologies can be implemented such as, for example, acquiring ultrasound image information of one or more hair-covered regions, fur-covered regions, and the like, during grooming. In an embodiment, the hair and scalp care system 500 includes a body structure 502 including a plurality of spaced-apart projections 504 configured to engage hair. In an embodiment, one or more of the spaced-apart projections 504 include a hair-covered surface contact region 506. For example, in an embodiment, one or more of the spaced-apart projections 504 include a scalp contact region. In an embodiment, the hair and scalp care system 500 includes an ultrasound image sensor component 508 forming part of the body structure 502.

In an embodiment, the ultrasound image sensor component 508 is operably coupled to one or more ultrasound transducers 510. In an embodiment, the hair and scalp care system 500 includes one or more ultrasound transducers 510. In an embodiment, the hair and scalp care system 500 includes one or more ultrasound transducers acoustically coupled to the scalp contact region of the spaced-apart projections. In an embodiment, the hair and scalp care system 500 includes one or more ultrasound transducers 510 forming part of the surface contact region 506 of the spaced-apart projections 504.

In an embodiment, the hair and scalp care system 500 is configured to find and identify scalp lesion based on ultrasound information associated with one or more scalp regions, hair-covered regions, fur-covered regions, and the like. See e.g., Wortsman, Ximena. *Sonography of the Primary Cutaneous Melanoma: A Review*, Radiology Research and Practice, Article ID 814396, July 2011. Web. 10 Dec. 2013, which is incorporated herein by reference. For example, in an embodiment, the body structure 502 is operably coupled to one or more ultrasound transducers 510 that are operable to interrogate one or more hair-covered regions with an ultrasonic stimulus and to acquire ultrasound images associated with one or more hair-covered regions during grooming. In an embodiment, one or more modules compare the acquired ultrasound images to reference image information such as reference ultrasound image information, reference ultrasound lesion images, previously acquired ultrasound images, user-specific ultrasound image information, cumulative ultrasound image information, and the like. In an embodiment, the one or more modules generate lesion identification information associated with the one or more hair-covered regions imaged during grooming based on the comparison.

In an embodiment, the hair and scalp care system 500 includes an ultrasound-imaging module 512. In an embodiment, the hair and scalp care system 500 includes an ultrasound-imaging module 512 operably coupled to the one or more ultrasound transducers 510. In an embodiment, the ultrasound-imaging module 512 is operable to transmit and receive ultrasound signals associated a scalp lesion.

In an embodiment, the ultrasound-imaging module 512 is configured to associate ultrasound signals from an ultrasound transducer 510 with scalp contact data from a corresponding spaced-apart projection. For example, in an embodiment, the ultrasound-imaging module 512 is configured to associate ultrasound signals from an ultrasound transducer 510 to determine whether the ultrasound transducer 510 is in contact with a hair-covered region, fur-covered region, and the like. In an embodiment, the ultrasound-imaging module 512 is configured to associate ultrasound signals from an ultrasound transducer 510 to determine a contact position of the ultrasound transducer 510 within a hair-covered region, fur-covered region, and the like. In an embodiment, the ultrasound-imaging module 512 is configured to assess whether the ultrasound transducer is in contact with a scalp region. In an embodiment, the ultrasound-imaging module 512 is configured to determine one or more parameters associated with a position of an ultrasound transducer within a scalp region.

In an embodiment, the ultrasound-imaging module 512 is operable to transmit and receive ultrasound signals to and from a scalp lesion. In an embodiment, the ultrasound-imaging module 512 is operable to acquire ultrasound information associated with a scalp lesion. In an embodiment, the ultrasound-imaging module 512 is operably coupled to a plurality of electromechanical transducer element. In an embodiment, the plurality of electromechanical transducer elements is configured to interrogate the scalp region with an ultrasonic stimulus. In an embodiment, the plurality of electromechanical transducer elements is configured to acquire an ultrasonic response associated with the scalp region interrogated with an ultrasonic stimulus.

In an embodiment, the ultrasound-imaging module 512 is configured to generate one or more of an ultrasound image, a color velocity Doppler mode image, or a power Doppler mode image of the scalp region. In an embodiment, the ultrasound-imaging module 512 is configured to generate a two-dimensional ultrasound imaging of the scalp region during grooming. In an embodiment, the ultrasound-imaging module 512 is configured to generate a three-dimensional ultrasound imaging of the scalp region during grooming.

In an embodiment, a scalp examination device includes a body structure 502 having a plurality of spaced-apart projections 504 configured to engage hair. In an embodiment, the scalp examination device includes circuitry 514 for interrogating one or more regions with an ultrasonic stimulus during grooming. For example, in an embodiment, the scalp examination device includes circuitry 514 for interrogating one hair-covered regions with an ultrasonic stimulus during grooming. In an embodiment, the scalp examination device includes circuitry 514 for interrogating one or more scalp regions with an ultrasonic stimulus during grooming. In an embodiment, the scalp examination device includes circuitry 516 for acquiring an ultrasonic response associated with interrogation of one or more scalp regions with the ultrasonic stimulus during grooming.

In an embodiment, the scalp examination device includes circuitry 518 for generating lesion classification information associated with the one or more scalp regions responsive to one or more inputs from the circuitry for acquiring an ultrasonic response. In an embodiment, the scalp examination device includes circuitry for 520 generating scalp lesion ultrasound information associated with the one or more scalp regions responsive to one or more inputs from the circuitry for acquiring an ultrasonic response. In an embodiment, the scalp examination device includes circuitry 522 for generating one or more of an ultrasound image, a color velocity Doppler mode image, or a power Doppler mode image of the one or more scalp regions. In an embodiment, the scalp examination device includes circuitry 524 for generating a three-dimensional ultrasound imaging of the one or more scalp regions during grooming. In an embodiment, the scalp examination device includes circuitry 526 for generating an ultrasound image of the one or more scalp regions responsive to one or more inputs from the circuitry for acquiring an ultrasonic response.

In an embodiment, the grooming system 400 includes a scalp lesion morphology module 120. In an embodiment, the scalp lesion morphology module 120 is operably coupled to one or more topographic sensors forming part of the brush structure 402. In an embodiment, the scalp lesion morphology module 120 is configured to determine a presence of scalp lesions responsive to one or more inputs from the one or more topographic sensors. In an embodiment, the grooming system 400 includes a scalp lesion dielectric module 130. In an embodiment, the scalp lesion dielectric module 130 is operably coupled to one or more impedance sensors forming part of the brush structure 402 and is configured to identify a scalp surface object based on a detected impendence obtained during grooming. In an embodiment, the hair and scalp care system 500 includes scalp lesion imaging module 140. In an embodiment, the scalp lesion imaging module 140 is operably coupled to one or more image sensors forming part of the sensor array 110 and is configured to identify a scalp surface object based on one or more images of a scalp region obtained during grooming.

In an embodiment, the hair and scalp care system 500 includes scalp lesion ultrasound imaging module 150. In an embodiment, the scalp lesion ultrasound imaging module 150 is operably coupled to one or more ultrasonic transducers forming part of the sensor array 110 and is configured to identify a scalp surface object based on one or more ultrasound images of a scalp region obtained during grooming In an embodiment, the hair and scalp care system 500 includes circuitry 212 for negotiating user-specific scalp lesion information based on at least one authentication protocol. For example, in an embodiment, the hair and scalp care system 500 includes circuitry 212 for negotiating user-specific scalp lesion information based on at least one cryptographic protocol, encryption protocol, or decryption protocol. In an embodiment, the grooming device 102 includes circuitry 214 for communicating with a remote enterprise and to receive control command information from the remote enterprise In an embodiment, the hair and scalp care system 500 includes circuitry 216 for actuating a discovery protocol that allows the grooming device and a remote enterprise to identify each other and to negotiate one or more pre-shared keys In an embodiment, the hair and scalp care system 500 includes circuitry 216 for actuating a discovery protocol that allows the system and a remote enterprise to identify each other and negotiate information.

Figure 6:
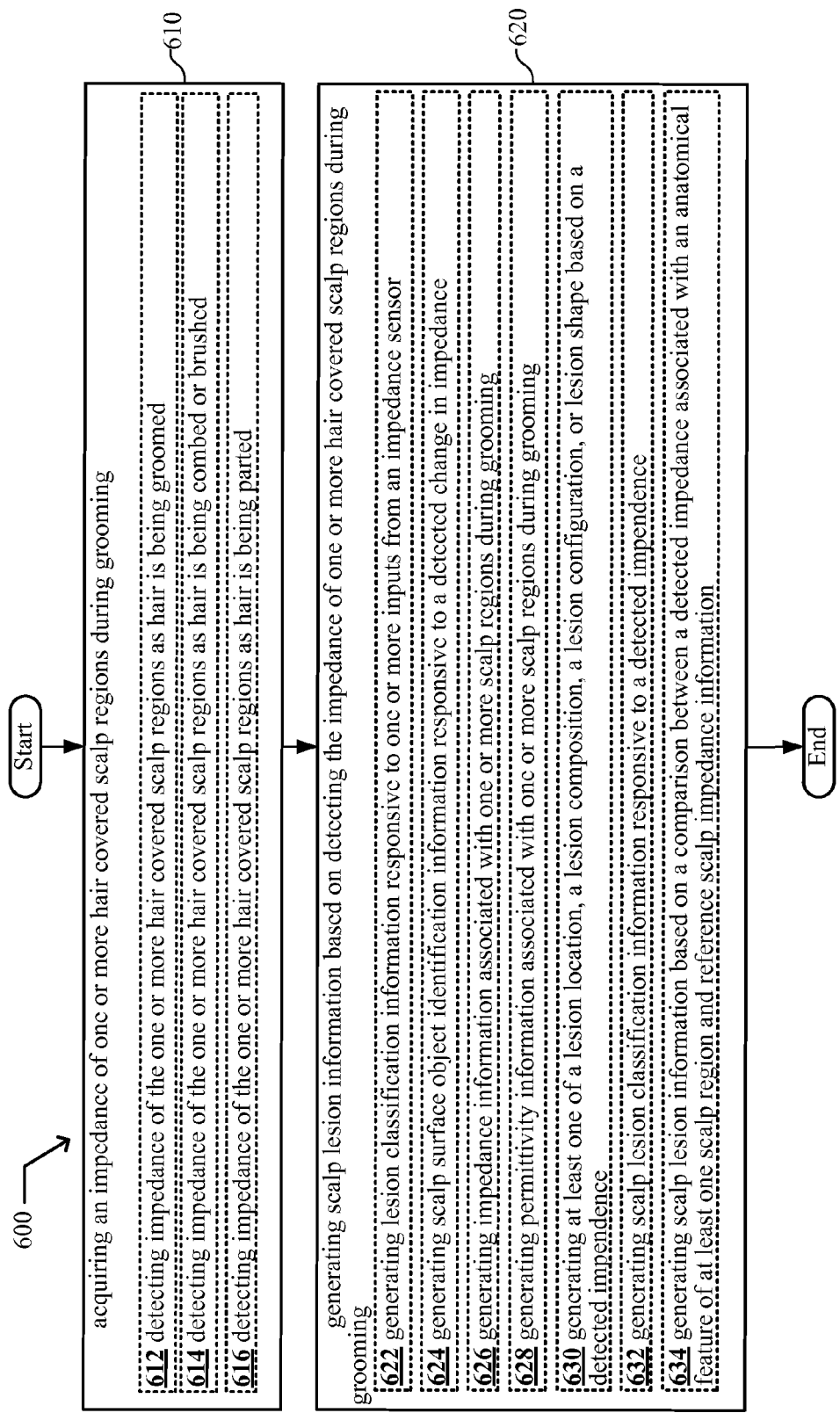
FIG. 6 shows a flow diagram of a method according to one embodiment.

FIG. 6 shows a method 600. At 610, the method 600 includes acquiring an impedance of one or more hair-covered scalp regions during grooming. At 612, acquiring the impedance of the one or more hair-covered scalp regions during grooming includes detecting impedance of the one or more hair-covered scalp regions as hair is being groomed. At 614, acquiring the impedance of the one or more hair-covered scalp regions during grooming includes detecting impedance of the one or more hair-covered scalp regions as hair is being combed or brushed. At 616, acquiring the impedance of the one or more hair-covered scalp regions during grooming includes detecting impedance of the one or more hair-covered scalp regions as hair is being parted.

In an embodiment, acquiring the impedance of the one or more hair-covered scalp regions during grooming includes detecting impedance of the one or more hair-covered scalp regions as a function of position of a grooming device 102 with respect to one or more reference positions. In an embodiment, acquiring the impedance of the one or more hair-covered scalp regions during grooming includes detecting impedance of the one or more hair-covered scalp regions as a function of position of a grooming device 102 with respect to one or more scalp regions. In an embodiment, acquiring the impedance of the one or more hair-covered scalp regions during grooming includes detecting impedance of the one or more hair-covered scalp regions as a function of position of a grooming device 102 with respect to one or more lesion locations.

At 620, the method 600 includes generating scalp lesion information based on detecting the impedance of one or more hair-covered scalp regions during grooming. At 622, generating scalp lesion information includes generating lesion classification information responsive to one or more inputs from an impedance sensor. At 624, generating scalp lesion information includes generating scalp surface object identification information responsive to a detected change in impedance. At 626, generating scalp lesion information includes generating impedance information associated with one or more scalp regions during grooming.

At 628, generating scalp lesion information includes generating dielectric permittivity information associated with one or more scalp regions during grooming. At 630, generating scalp lesion information includes generating at least one of a lesion location, a lesion composition, a lesion configuration, or lesion shape based on a detected impendence. At 632, generating scalp lesion information includes generating scalp lesion classification information responsive to a detected impendence. At 634, generating scalp lesion information includes generating scalp lesion information based on a comparison between a detected impedance associated with an anatomical feature of at least one scalp region and reference scalp impedance information.

Figure 7:
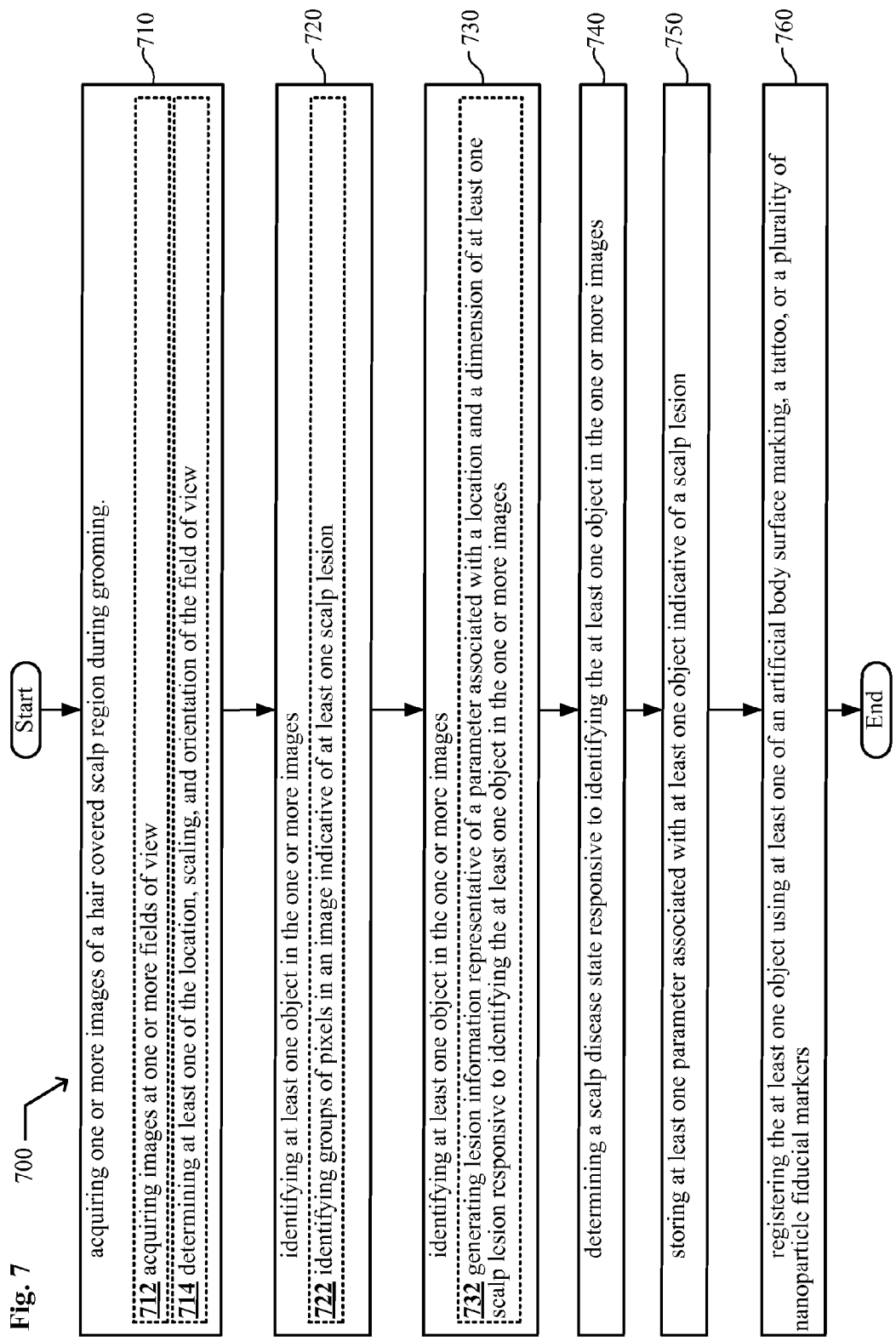
FIG. 7 shows a flow diagram of a grooming method according to one embodiment.

FIG. 7 shows a grooming method 700. At 710, the grooming method 700 includes acquiring one or more images of a hair-covered scalp region during grooming. At 712, acquiring the one or more images of the hair-covered scalp region during grooming includes acquiring images at one or more fields of view. At 714, acquiring images at one or more fields of view comprises determining at least one of the location, scaling, and orientation of the field of view.

At 720, the grooming method 700 includes identifying at least one object in the one or more images. At 722, identifying the at least one object in the one or more images includes identifying groups of pixels in an image indicative of at least one scalp lesion. At 730, the grooming method 700 includes generating scalp lesion information responsive to identifying at least one object in the one or more images. At 732, generating scalp lesion information includes generating lesion information representative of a parameter associated with a location and a dimension of at least one scalp lesion responsive to identifying the at least one object in the one or more images. At 740, the grooming method 700 includes determining a scalp disease state responsive to identifying the at least one object in the one or more images. At 750, the grooming method 700 includes storing at least one parameter associated with at least one object indicative of a scalp lesion. At 760, the grooming method 700 includes registering the at least one object using at least one of an artificial body surface marking, a tattoo, or a plurality of nanoparticle fiducial markers.

FIG. 8 shows a method 800. At 810, the method 800 includes interrogating one or more hair-covered scalp regions with an ultrasonic stimulus during grooming. At 820, the method 800 includes detecting an ultrasonic response associated with interrogating the one or more scalp regions with the ultrasonic stimulus.

At 830, the method 800 includes generating scalp lesion information. At 832, generating the scalp lesion information includes generating primary lesion information responsive to one or more inputs indicative of an ultrasonic response. At 834, generating the scalp lesion information includes generating secondary lesion information responsive to one or more inputs indicative of an ultrasonic response. At 836, generating the scalp lesion information includes generating lesion shape information responsive to one or more inputs indicative of an ultrasonic response. At 838, generating the scalp lesion information includes generating lesion configuration information responsive to one or more inputs indicative of an ultrasonic response.

At 840, generating the scalp lesion information includes generating lesion border information responsive to one or more ultrasonic inputs indicative of an ultrasonic response. At 842, generating the scalp lesion information includes generating classification information associated with a scalp lesion responsive to one or more inputs associated with the detected ultrasonic response. At 844, generating the scalp lesion information includes generating scalp lesion ultrasound information associated with the one or more scalp regions responsive to one or more inputs associated with the detected ultrasonic response.

At 846, generating the scalp lesion information includes generating one or more of an ultrasound image, a color velocity Doppler mode image, and a power Doppler mode image of the one or more scalp regions responsive to one or more inputs associated with the detected ultrasonic response. At 848, generating the scalp lesion information includes generating a three-dimensional ultrasound imaging of the one or more scalp regions responsive to one or more inputs associated with the detected ultrasonic response.

Figure 9A:
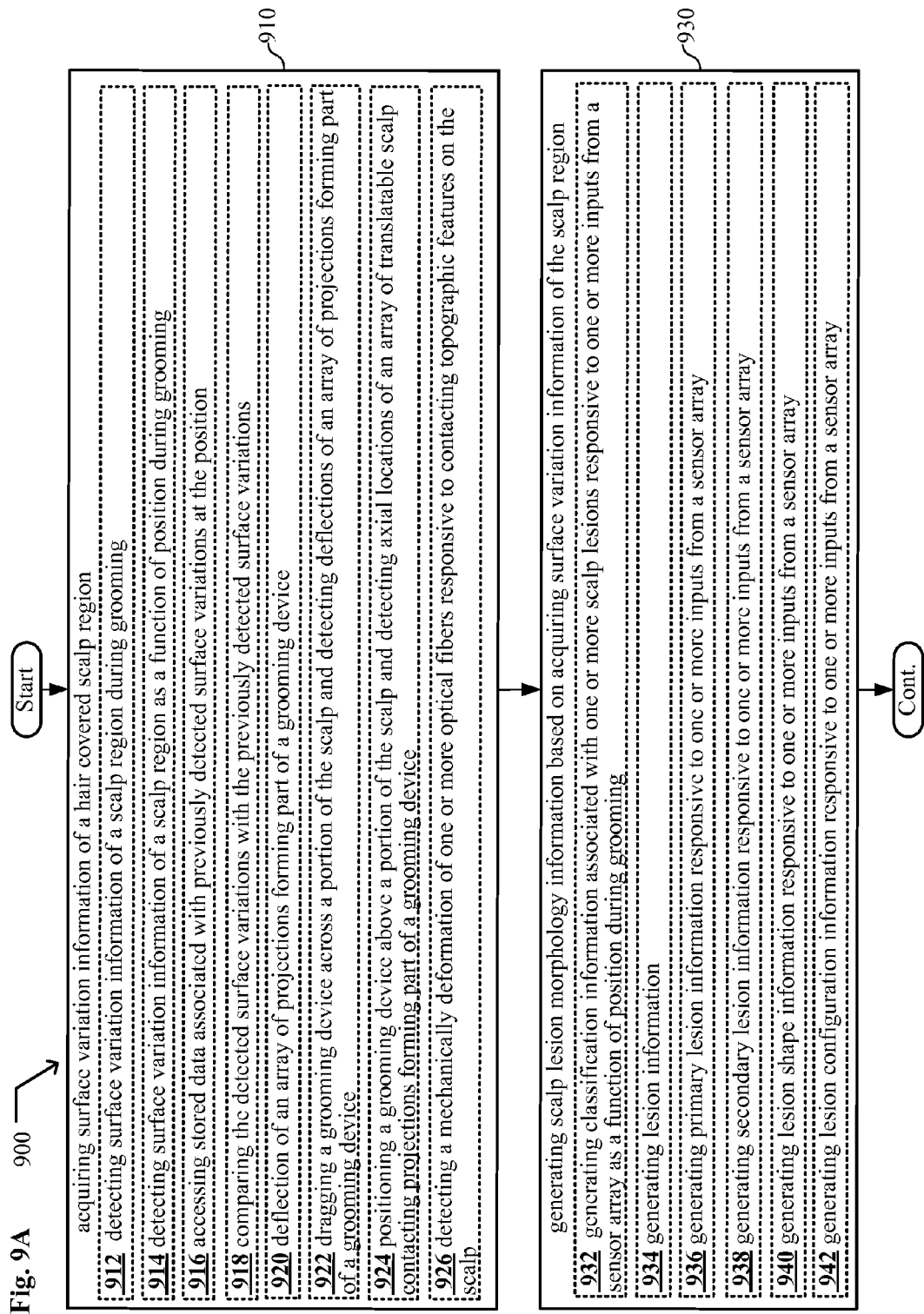
FIGS. 9A and 9B show a flow diagram of a method according to one embodiment
Figure 9B:
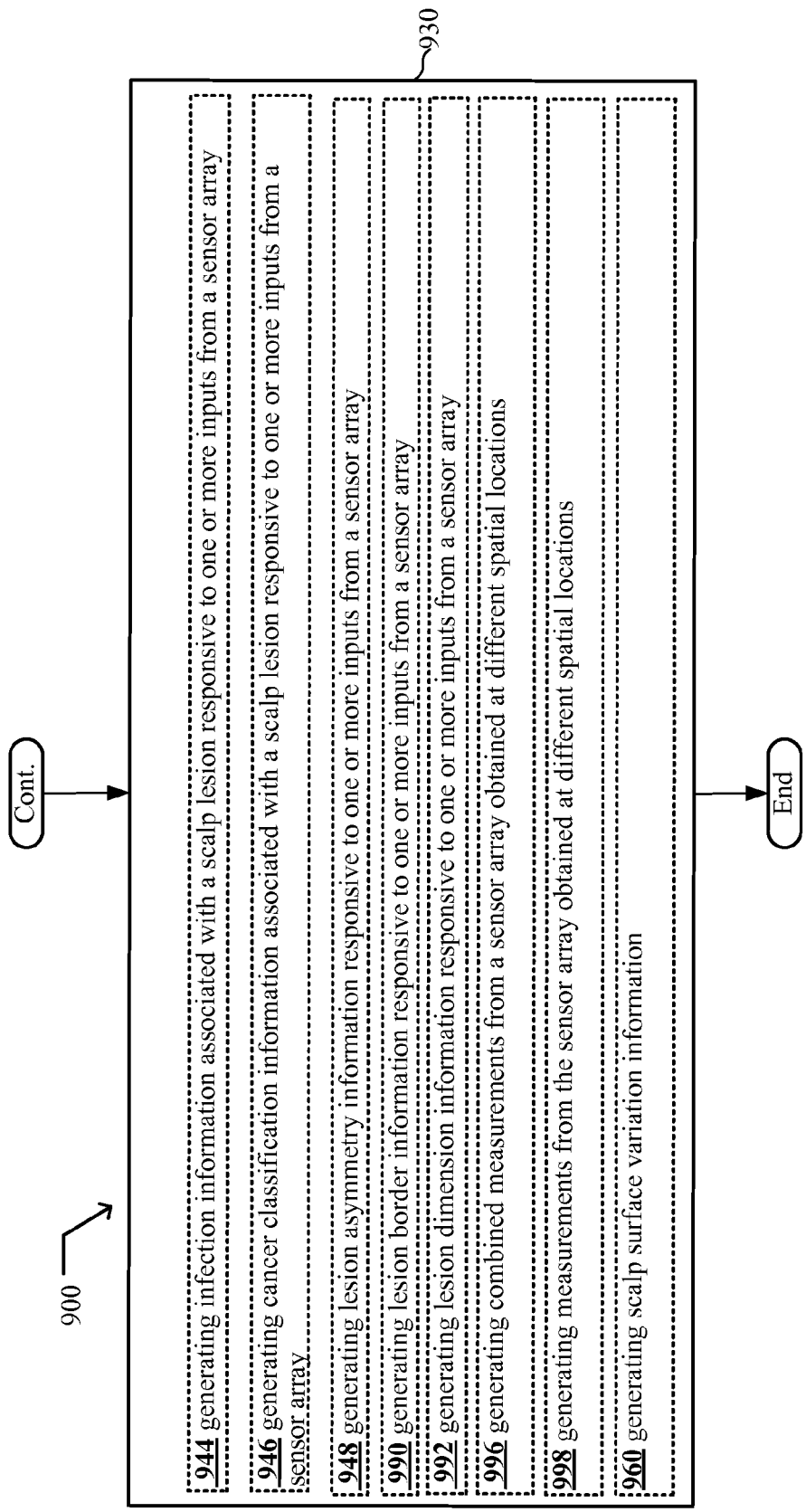

FIG. 9 shows a method 900. At 910, the method 900 includes acquiring surface variation information of a hair-covered scalp region. At 912, acquiring surface variation information of the scalp region includes detecting surface variation information of a scalp region during grooming. At 914, acquiring surface variation information of the scalp region includes detecting surface variation information of a scalp region as a function of position during grooming. In an embodiment, acquiring surface variation information of the scalp region includes storing the detected surface variation information of a scalp region as a function of position. At 916, acquiring surface variation information of the scalp region includes accessing stored data associated with previously detected surface variations at the position.

At 918, acquiring surface variation information of the scalp region includes comparing the detected surface variations with previously detected surface variations. At 920, acquiring surface variation information of the scalp region includes detecting a deflection of an array of projections forming part of a grooming device. In an embodiment, acquiring surface variation information of the scalp region includes detecting a deflection of an array of flexible projections forming part of a grooming device. In an embodiment, acquiring surface variation information of the scalp region includes relative displacement of an array of rigid projections forming part of a grooming device At 922, acquiring surface variation information of the scalp region includes dragging a grooming device across a portion of the scalp and detecting deflections of an array of projections forming part of a grooming device 102. At 924, acquiring surface variation information of the scalp region includes positioning a grooming device above a portion of the scalp and detecting axial locations of an array of translatable scalp contacting projections forming part of a grooming device. At 926, acquiring surface variation information of the scalp region includes detecting a mechanically deformation of one or more optical fibers responsive to contacting topographic features on the scalp.

At 930, the method 900 includes generating scalp lesion morphology information based on acquiring surface variation information of the scalp region. At 932, generating the scalp lesion morphology information includes generating classification information associated with one or more scalp lesions responsive to one or more inputs from a sensor array 110 as a function of position during grooming. At 934, generating the scalp lesion morphology information includes generating lesion information.

At 936, generating the scalp lesion morphology information includes generating primary lesion information responsive to one or more inputs from a sensor array 110. At 938, generating the scalp lesion morphology information includes generating secondary lesion information responsive to one or more inputs from a sensor array 110. At 940, generating the scalp lesion morphology information includes generating lesion shape information responsive to one or more inputs from a sensor array 110.

At 942, generating the scalp lesion morphology information includes generating lesion configuration information responsive to one or more inputs from a sensor array 110. At 944, generating the scalp lesion morphology information includes generating infection information associated with a scalp lesion responsive to one or more inputs from a sensor array 110. At 946, generating the scalp lesion morphology information includes generating cancer classification information associated with a scalp lesion responsive to one or more inputs from a sensor array 110. At 948, generating the scalp lesion morphology information includes generating lesion asymmetry information responsive to one or more inputs from a sensor array 110.

At 990, generating the scalp lesion morphology information includes generating lesion border information responsive to one or more inputs from a sensor array 110. At 992, generating the scalp lesion morphology information includes generating lesion dimension information responsive to one or more inputs from a sensor array 110. At 994, generating the scalp lesion morphology information includes generating lesion rate of change information responsive to one or more inputs from a sensor array 110.

At 996, generating the scalp lesion morphology information includes generating combined measurements from a sensor array 110 obtained at different spatial locations. At 998, generating the scalp lesion morphology information includes generating measurements from the sensor array 110 obtained at different spatial locations. At 960, generating the scalp lesion morphology information includes generating scalp surface variation information. In an embodiment, the method 900 includes comprising releasing a marker to the scalp region. In an embodiment, the method 900 includes detecting a previously released marker within the scalp region.

It is noted that FIGS. 6-9B denotes "start" and "end" positions. However, nothing herein should be construed to indicate that these are limiting and it is contemplated that other or additional steps or functions can occur before or after those described in FIGS. 6-9B.

The claims, description, and drawings of this application may describe one or more of the instant technologies in operational/functional language, for example as a set of operations to be performed by a computer. Such operational/functional description in most instances can be specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions are representative of static or sequenced specifications of various hardware elements. This is true because tools available to implement technical disclosures set forth in operational/functional formats— tools in the form of a high-level programming language (e.g., C, java, visual basic), etc.), or tools in the form of Very high speed Hardware Description Language ("VIDAL," which is a language that uses text to describe logic circuits—)—are generators of static or sequenced specifications of various hardware configurations. This fact is sometimes obscured by the broad term "software," but, as shown by the following explanation, what is termed "software" is a shorthand for a massively complex interchanging/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, available at the website en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, available at the website en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct" (e.g., that "software"—a computer program or computer—programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In an embodiment, if a high-level programming language is the tool used to implement a technical disclosure in the form of functions/operations, it can be understood that, far from being abstract, imprecise, "fuzzy," or "mental" in any significant semantic sense, such a tool is instead a near incomprehensibly precise sequential specification of specific computational—machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory devices, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, available at the website en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, available at the website en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, available at the website en.wikipedia.org/wiki/Instructions_per_second (as of Jun. 5, 2012, 21:04 GMT).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. Accordingly, any such operational/functional technical descriptions may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, it can be recognizes that a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

At least a portion of the devices or processes described herein can be integrated into an information processing system. An information processing system generally includes one or more of a system unit housing, a video display device, memory, such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), or control systems including feedback loops and control motors (e.g., feedback for detecting position or velocity, control motors for moving or adjusting components or quantities). An information processing system can be implemented utilizing suitable commercially available components, such as those typically found in data computing/communication or network computing/communication systems.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Various vehicles by which processes or systems or other technologies described herein can be effected (e.g., hardware, software, firmware, etc., in one or more machines or articles of manufacture), and that the preferred vehicle will vary with the context in which the processes, systems, other technologies, etc., are deployed. For example, if an implementer determines that speed and accuracy are paramount, the implementer may opt for a mainly hardware or firmware vehicle; alternatively, if flexibility is paramount, the implementer may opt for a mainly software implementation that is implemented in one or more machines or articles of manufacture; or, yet again alternatively, the implementer may opt for some combination of hardware, software, firmware, etc. in one or more machines or articles of manufacture. Hence, there are several possible vehicles by which the processes, devices, other technologies, etc., described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. In an embodiment, optical aspects of implementations will typically employ optically-oriented hardware, software, firmware, etc., in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable, physically interacting components, wirelessly interactable, wirelessly interacting components, logically interacting, logically interactable components, etc.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components, or inactive-state components, or standby-state components, unless context requires otherwise.

The foregoing detailed description has set forth various embodiments of the devices or processes via the use of block diagrams, flowcharts, or examples. Insofar as such block diagrams, flowcharts, or examples contain one or more functions or operations, it will be understood by the reader that each function or operation within such block diagrams, flowcharts, or examples can be implemented, individually or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or, "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A hair and scalp care system, comprising:
    a body structure including a plurality of spaced-apart projections configured to engage hair, one or more of the spaced-apart projections having a scalp contact region;
    one or more ultrasound transducers acoustically coupled to the scalp contact region of the spaced-apart projections;
    an ultrasound-imaging module including computing device circuitry and memory circuitry, the ultrasound-imaging module operably coupled to the one or more ultrasound transducers, the ultrasound-imaging module operable to transmit and receive ultrasound signals associated with a scalp lesion;
    a scalp lesion morphology module including computing device circuitry and memory circuitry, the scalp lesion morphology module operably coupled to the ultrasound transducers and configured to generate, responsive to one or more inputs from the one or more ultrasound transducers, a tactile response for delivery to a user; and
    an output component operably coupled to the scalp lesion morphology module and configured to deliver the tactile response to the user.

2. The hair and scalp care system of claim 1, wherein one or more of the ultrasound transducers form part of one or more of the plurality of spaced-apart projections.

3. The hair and scalp care system of claim 1, wherein the ultrasound-imaging module is operable to acquire ultrasound information associated with the scalp lesion.

4. The hair and scalp care system of claim 1, wherein the one or more ultrasound transducers include a plurality of electromechanical transducer elements, the plurality of electromechanical transducer elements configured to interrogate the scalp region with an ultrasonic stimulus.

5. The hair and scalp care system of claim 1, wherein the ultrasound-imaging module is configured to generate one or more of an ultrasound image, a color velocity Doppler mode image, or a power Doppler mode image of the scalp region.

6. The hair and scalp care system of claim 1, wherein the ultrasound-imaging module is configured to generate a three-dimensional ultrasound image of the scalp region during grooming.

7. The hair and scalp care system of claim 1, wherein the ultrasound-imaging module is configured to compare ultrasound images with previously acquired ultrasound images in real time.

8. The hair and scalp care system of claim 1, including
    one or more accelerometers, inclinometers, or gyroscopes forming part of the body structure; and
    an inertial navigation module operably coupled to the body structure and to the one or more accelerometers, inclinometers, or gyroscopes, the inertial navigation module including computing device circuitry and memory circuitry, wherein the inertial navigation module is configured to use the one or more accelerometers, inclinometers, or gyroscopes to generate information indicative of a location and orientation of a portion of the hair and scalp care system.

9. The hair and scalp care system of claim 1, including
    one or more impedance sensors forming part of the body structure; and
    a scalp lesion dielectric module operably coupled to the one or more impedance sensors and including computing device circuitry and memory circuitry, the scalp lesion dielectric module configured to identify a scalp surface object based on a detected impedance obtained during grooming.

10. The hair and scalp care system of claim 1, including
    a sensor array forming part of the body structure, the sensor array including one or more sensor elements; and
    a scalp lesion morphology module operably connected to the sensor array and including computing device circuitry and memory circuitry, wherein the scalp lesion morphology module is configured to determine a presence of a scalp lesion responsive to one or more inputs from the sensor array.

11. The hair and scalp care system of claim 1, including
a sensor array forming part of the body structure, the sensor array including one or more image sensors; and
a scalp lesion imaging module operably connected to the sensor array and including computing device circuitry and memory circuitry, wherein the scalp lesion imaging module is configured to identify a scalp surface object based on one or more images of a scalp region obtained during grooming.

12. The hair and scalp care system of claim 1, including
a scalp examination module including computing device circuitry and memory circuitry, the scalp examination module operably coupled to the ultrasound-imaging module and configured to determine cumulative lesion examination information based on at least one output from the ultrasound imaging module.

13. The hair and scalp care system of claim 12, wherein the scalp examination module includes one or more memory devices having user-specific lesion data stored thereon.

14. The hair and scalp care system of claim 1, including
one or more marker-dispenser components; and
an examined region module operably coupled to the one or more marker-dispenser components and including computing device circuitry and memory circuitry, the examined region module configured to activate release of one or more marker or dye particles by the marker dispenser components.

15. The hair and scalp care system of claim 14, wherein the examined region module is configured to activate release of a marker to mark examined regions during grooming.

16. The hair and scalp care system of claim 14, wherein the one or more marker-dispenser components are operably coupled to one or more of the plurality of spaced-apart projections.

17. The hair and scalp care system of claim 14, wherein the examined region module is operable to detect a marker previously released by at least one of the one or more marker-dispenser components.

18. The hair and scalp care system of claim 1, wherein the scalp lesion morphology module is configured to generate scalp lesion morphology information responsive to the one or more inputs from the one or more ultrasound transducers, and wherein the tactile response is indicative of the scalp lesion morphology information.

19. The hair and scalp care system of claim 1, wherein the tactile response is indicative of a user instruction.

20. The hair and scalp care system of claim 19, wherein the tactile response is indicative of a user instruction instructing the user to perform at least one of second pass, a slower pass, a static inspection, a re-inspection with different imaging modality, re-grooming, and grooming using a different imaging modality.

21. A scalp examination device, comprising:
a body structure having a plurality of spaced-apart projections configured to engage hair;
one or more electromechanical transducer elements acoustically coupled to one or more scalp contact regions of one or more of the plurality of spaced-apart projections;
one or more contact sensors forming part of the body structure and configured to sense skin contact by one or more scalp contact regions of one or more of the plurality of spaced-apart projections;
circuitry for interrogating one or more scalp regions with an ultrasonic stimulus delivered from one or more of the electromechanical transducer elements via one or more scalp contact regions of one or more of the plurality of spaced-apart projections during grooming;
circuitry for assessing whether one or more scalp contact regions of one or more of the spaced-apart projections are in contact with the one or more scalp regions;
circuitry for acquiring an ultrasonic response via one or more of the electromechanical transducer elements responsive to an indication that one or more scalp contact region of the one or more spaced-apart projections is in contact with the one or more scalp regions, the ultrasonic response associated with interrogation of the one or more scalp regions with the ultrasonic stimulus during grooming; and
a scalp lesion morphology module including computing device circuitry and memory circuitry, the scalp lesion morphology module operably coupled to the one or electromechanical transducer elements and configured to generate scalp lesion morphology information associated with the one or more scalp regions responsive to the ultrasonic response.

22. The scalp examination device of claim 21, including
circuitry for generating lesion classification information associated with the one or more scalp regions responsive to one or more inputs from the circuitry for acquiring an ultrasonic response by comparing information associated with the ultrasonic response with reference lesion classification information.

23. The scalp examination device of claim 21, including
circuitry for generating scalp lesion ultrasound information associated with the one or more scalp regions responsive to one or more inputs from the circuitry for acquiring an ultrasonic response by comparing information associated with the ultrasonic response with reference lesion ultrasound information.

24. The scalp examination device of claim 21, including
circuitry for generating one or more of an ultrasound image, a color velocity Doppler mode image, or a power Doppler mode image of the one or more scalp regions responsive to one or more inputs from the circuitry for acquiring the ultrasonic response.

25. The scalp examination device of claim 21, including
circuitry for generating a three-dimensional ultrasound image of the one or more scalp regions during grooming responsive to one or more inputs from the circuitry for acquiring the ultrasonic response.

26. The scalp examination device of claim 21, including
circuitry for generating an ultrasound image of the one or more scalp regions responsive to one or more inputs from the circuitry for acquiring the ultrasonic response.

27. The scalp examination device of claim 21, wherein the one or more contact sensors are dimensioned and configured to deflect responsive to contacting topographic features on the scalp during grooming.

28. The scalp examination device of claim 21, wherein the one or more contact sensors are dimensioned and configured to be displaced along a longitudinal axis responsive to contacting topographic features on the scalp during grooming.

29. The scalp examination device of claim 21, wherein the one or more contact sensors include one or more pressure sensors, capacitance sensors, flexure sensors, strain sensors, or optical sensors.

30. A method, comprising:
interrogating one or more hair-covered scalp regions with an ultrasonic stimulus during grooming with a scalp examination device, the scalp examination device including a body structure having a plurality of spaced-apart projections configured to engage hair, one or more electromechanical transducer elements acoustically coupled to one or more scalp contact regions of one or more of the plurality of spaced-apart projections and configured to interrogate the one or more hair-covered scalp regions with the ultrasonic stimulus, one or more contact sensors configured to sense skin contact by one or more scalp contact regions of one or more of the plurality of spaced-apart projection, an output component configured to deliver a tactile response to the user, a scalp lesion morphology module operably connected to the one or more electromechanical transducer elements and configured to generate the tactile response, and computing device circuitry and memory circuitry operably coupled to the one or more electromechanical transducer elements and one or more contact sensors;

sensing via the one or more contact sensors skin contact by the one or more scalp contact regions of one or more of the plurality of spaced-apart projections;

detecting via the one or more of the electromechanical transducer elements acoustically coupled to the one or more scalp contact regions, responsive to sensing via the one or more contact sensors skin contact by the one or more scalp contact regions of one or more of the plurality of spaced-apart projections, an ultrasonic response associated with interrogating the one or more scalp regions with the ultrasonic stimulus;

generating scalp lesion information associated with the one or more scalp regions with the computing device circuitry responsive to one or more inputs indicative of the ultrasonic response;

generating the tactile response with the scalp lesion morphology module, responsive to one or more inputs from the one or more electromechanical transducer elements; and delivering the tactile response to the user via the output component.

31. The method of claim 30, wherein generating the scalp lesion information includes generating primary lesion information responsive to the one or more inputs indicative of an ultrasonic response.

32. The method of claim 30, wherein generating the scalp lesion information includes generating secondary lesion information responsive to the one or more inputs indicative of an ultrasonic response.

33. The method of claim 30, wherein generating the scalp lesion information includes generating lesion configuration information responsive to the one or more inputs indicative of an ultrasonic response.

34. The method of claim 30, wherein generating the scalp lesion information includes generating scalp lesion ultrasound information associated with the one or more scalp regions responsive to one or more inputs associated with the detected ultrasonic response.

35. The method of claim 30, wherein generating the scalp lesion information includes generating one or more of an ultrasound image, a color velocity Doppler mode image, and a power Doppler mode image of the one or more scalp regions responsive to one or more inputs associated with the detected ultrasonic response.

36. The method of claim 30, wherein generating the scalp lesion information includes generating a three-dimensional ultrasound image of the one or more scalp regions responsive to one or more inputs associated with the detected ultrasonic response.

37. A method, comprising:

interrogating one or more hair-covered scalp regions with an ultrasonic stimulus during grooming with a hair and scalp care system, the hair and scalp care system including a body structure having a plurality of spaced-apart projections configured to engage hair, one or more ultrasound transducers acoustically coupled to one or more scalp contact regions of one or more of the plurality of spaced-apart projections and configured to interrogate the one or more hair-covered scalp regions with the ultrasonic stimulus, an output component configured to deliver a tactile response to a user, and computing device circuitry and memory circuitry including an ultrasound imaging module operable to transmit and receive ultrasound signals associated with the scalp region via the one or more ultrasound transducers, and a scalp lesion morphology module configured to generate a tactile response for delivery to the user;

sensing with the ultrasound imaging module, via the one or more ultrasound transducers, an ultrasound signal associated with a scalp lesion;

generating with the scalp lesion morphology module, responsive to one or more inputs from the one from the one or more ultrasound transducers, a tactile response; and delivering, via the output component, the tactile response to the user.

* * * * *